(12) United States Patent
Shekalim

(10) Patent No.: US 8,992,503 B2
(45) Date of Patent: Mar. 31, 2015

(54) MINIATURE IMPLANTED DRUG DELIVERY DEVICES AND INSERTER SYSTEMS FOR INTRODUCING SUCH DEVICES

(75) Inventor: Avraham Shekalim, Nesher (IL)

(73) Assignee: Microsert Ltd., Yokneam Hamoshava (IL)

( * ) Notice: Subject to any disclaimer, the term of this patent is extended or adjusted under 35 U.S.C. 154(b) by 0 days.

(21) Appl. No.: 14/004,683

(22) PCT Filed: Mar. 27, 2012

(86) PCT No.: PCT/IB2012/051462
§ 371 (c)(1),
(2), (4) Date: Sep. 12, 2013

(87) PCT Pub. No.: WO2012/131583
PCT Pub. Date: Oct. 4, 2012

(65) Prior Publication Data
US 2014/0018771 A1    Jan. 16, 2014

Related U.S. Application Data

(60) Provisional application No. 61/468,014, filed on Mar. 27, 2011.

(51) Int. Cl.
*A61F 9/00* (2006.01)
*A61M 5/32* (2006.01)
*A61M 5/142* (2006.01)

(52) U.S. Cl.
CPC ........... *A61F 9/0017* (2013.01); *A61M 5/3297* (2013.01); *A61M 5/14276* (2013.01)
USPC ........................... 604/506; 604/218; 604/187

(58) Field of Classification Search
CPC .......... A61F 9/0017; A61F 2250/0003; A61K 9/0051; A61M 5/1428
USPC .......................................... 604/187, 218, 506
See application file for complete search history.

(56) References Cited

U.S. PATENT DOCUMENTS

| | | |
|---|---|---|
| 4,351,337 A | 9/1982 | Sidman |
| 4,428,397 A | 1/1984 | Bron |
| 4,450,150 A | 5/1984 | Sidman |
| 4,820,273 A | 4/1989 | Reinickie |
| 5,061,242 A | 10/1991 | Sampson |
| 5,163,920 A | 11/1992 | Olive |
| 5,824,072 A | 10/1998 | Wong |
| 5,836,935 A | 11/1998 | Ashton |
| 5,972,369 A | 10/1999 | Roorda |

(Continued)

FOREIGN PATENT DOCUMENTS

| | | |
|---|---|---|
| WO | 2009037384 | 3/2009 |
| WO | 2010028310 | 3/2010 |

*Primary Examiner* — Nicholas Lucchesi
*Assistant Examiner* — Anh Bui
(74) *Attorney, Agent, or Firm* — Mark M. Friedman

(57) ABSTRACT

A system (10, 200) and corresponding method for introducing a drug delivery device (18, 218) through at least part of a biological barrier starts with the drug delivery device (18, 218) deployed within a channel of a hollow needle (12, 212). The hollow needle is inserted into the biological barrier and the drug delivery device is pushed forward by a suitable plunger. The drug delivery device is preferably anchored to the biological barrier through a radially expanding retention arrangement (36, 36', 36a), and is preferably filled with a liquid drug after deployment via a filling needle (24, 222) extending within the channel of the hollow needle (12, 212).

10 Claims, 21 Drawing Sheets

(56) References Cited

U.S. PATENT DOCUMENTS

| | | |
|---|---|---|
| 5,993,414 A | 11/1999 | Haller |
| 6,183,461 B1 | 2/2001 | Matsuura et al. |
| 6,331,313 B1 | 12/2001 | Wong |
| 6,719,750 B2 | 4/2004 | Varner |
| 7,361,168 B2 | 4/2008 | Makower |
| 7,563,255 B2 | 7/2009 | Adamis |
| 7,641,688 B2 * | 1/2010 | Lesh .................... 623/11.11 |
| 2009/0264813 A1 * | 10/2009 | Chang .................... 604/60 |
| 2010/0010468 A1 | 1/2010 | Becker |
| 2010/0255061 A1 * | 10/2010 | de Juan et al. ............... 424/427 |

* cited by examiner

FIG. 1A
FIG. 1B
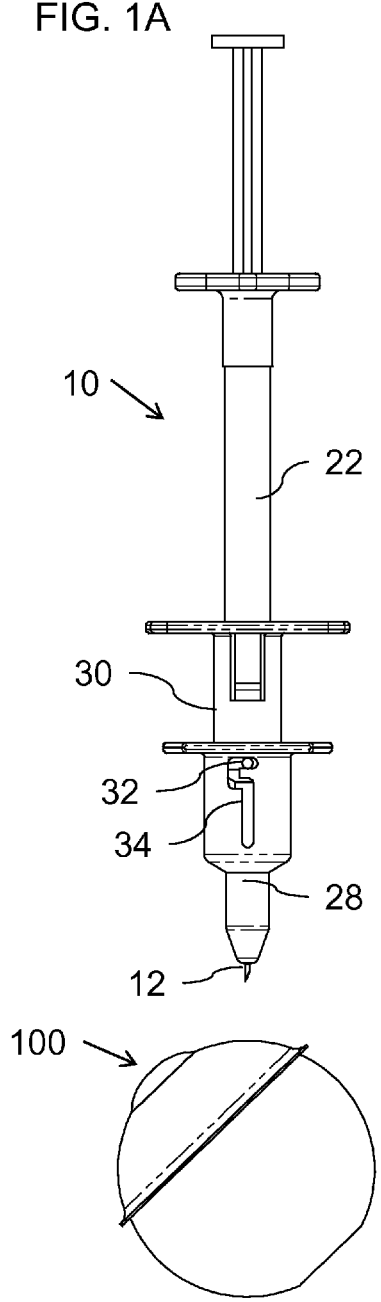
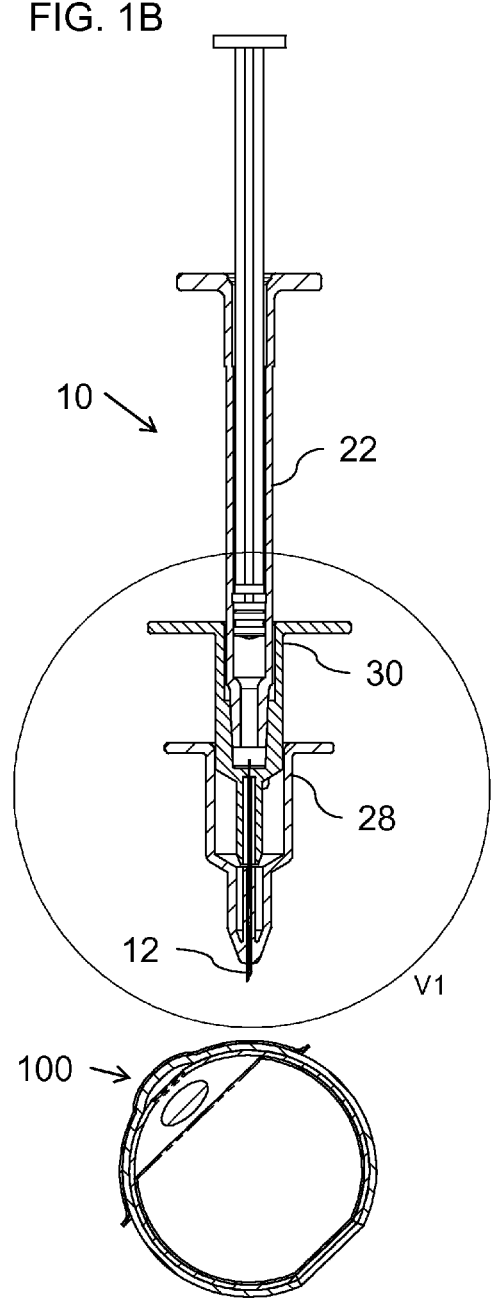

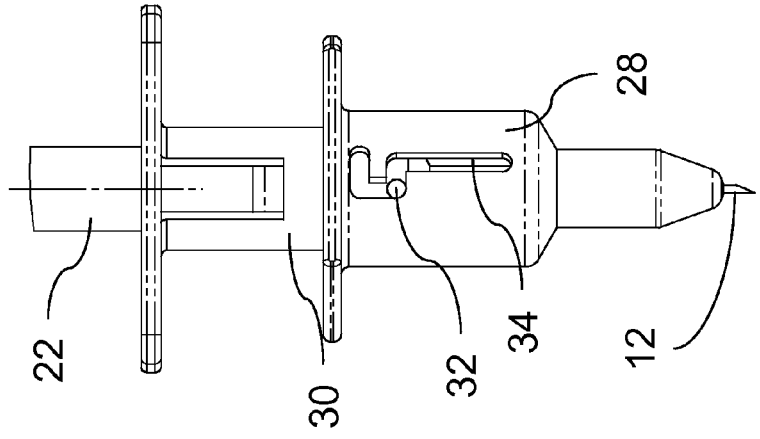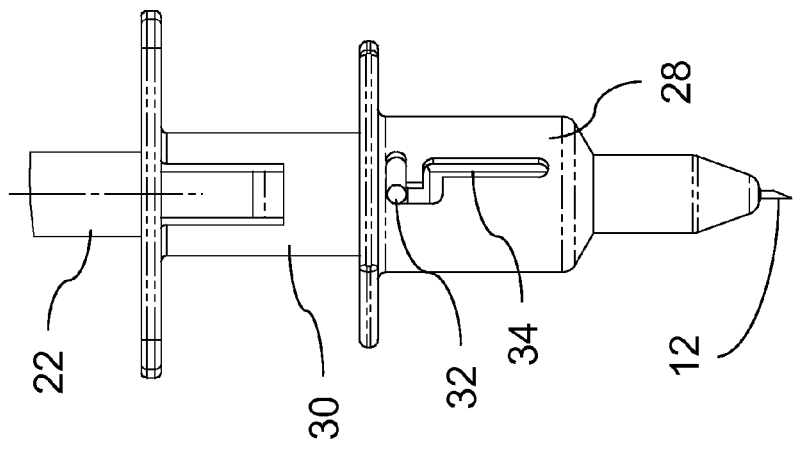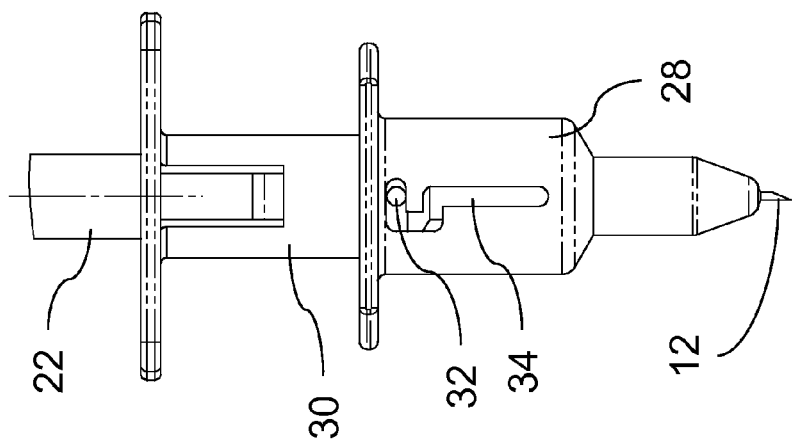

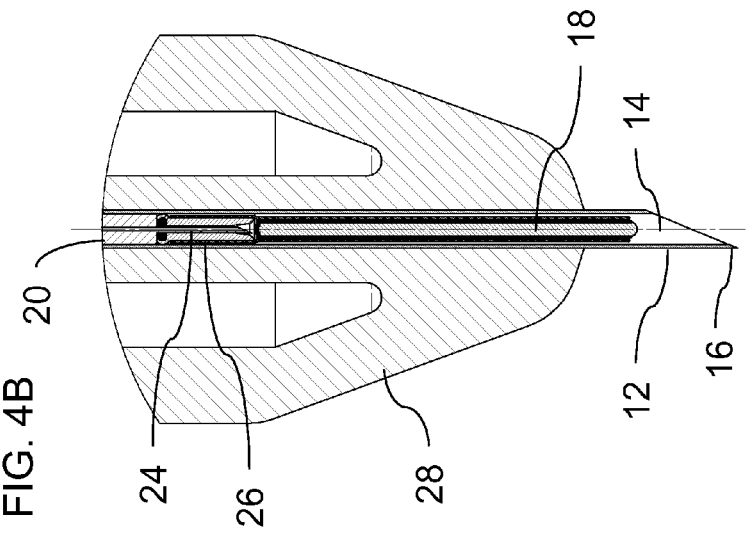
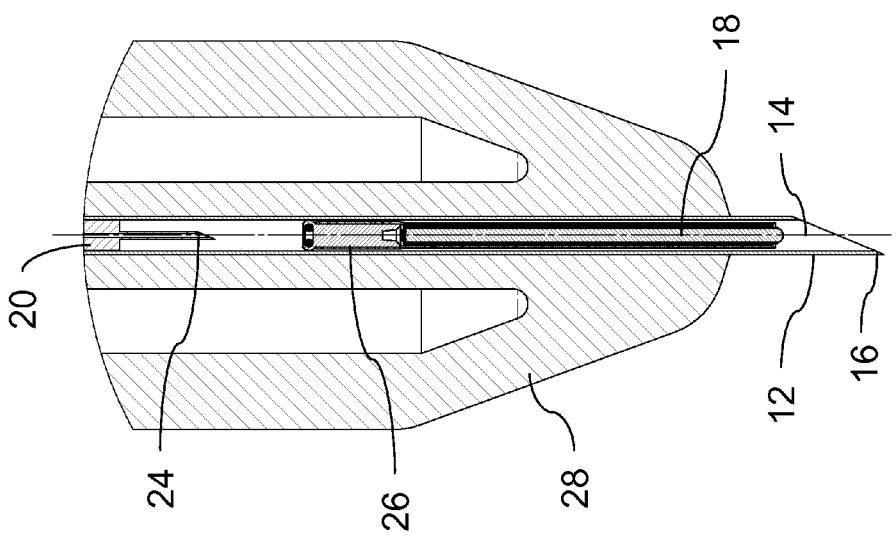

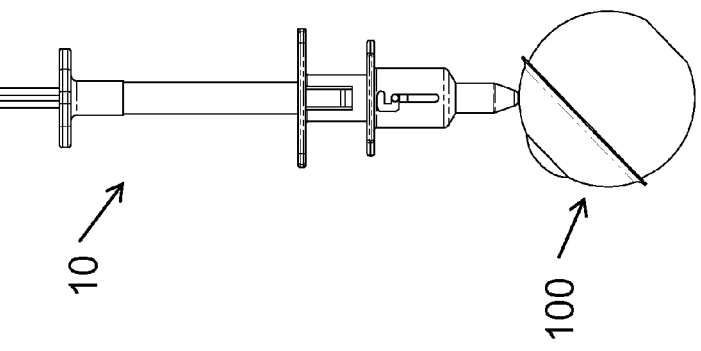
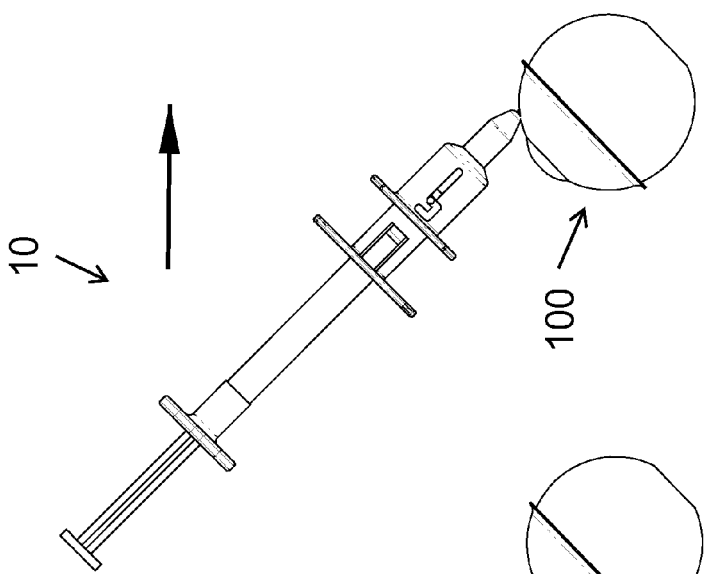
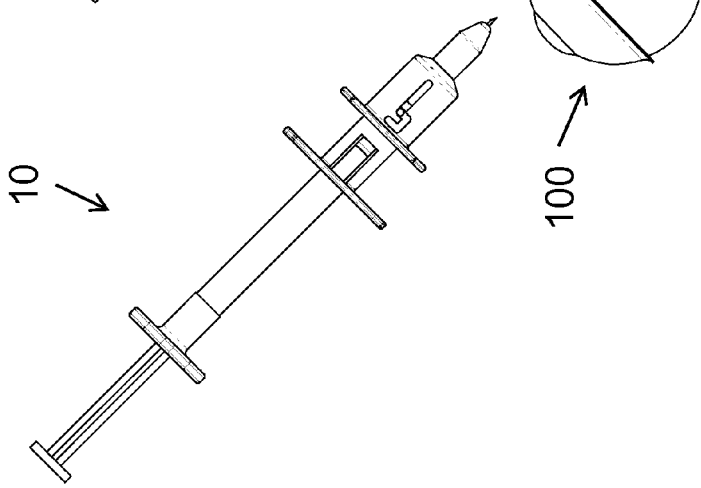

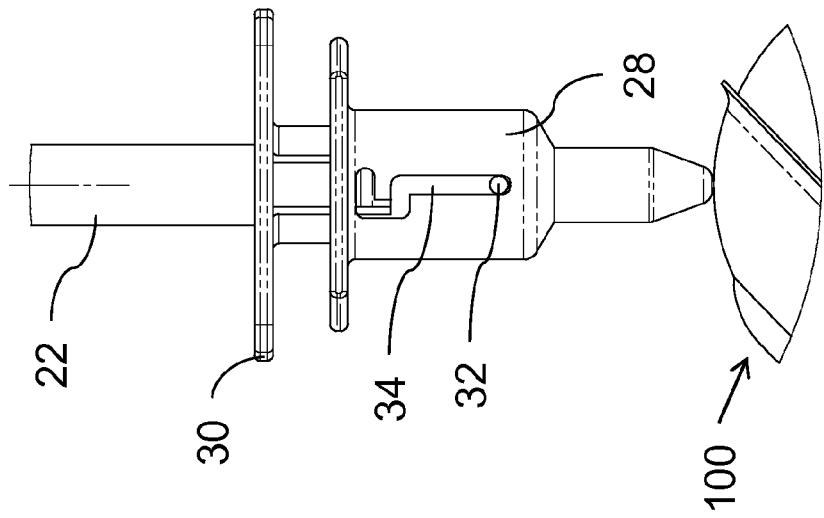
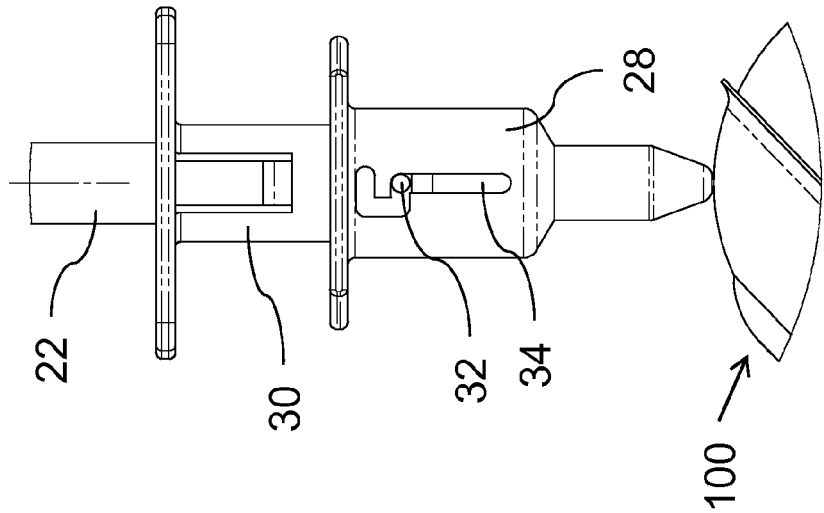

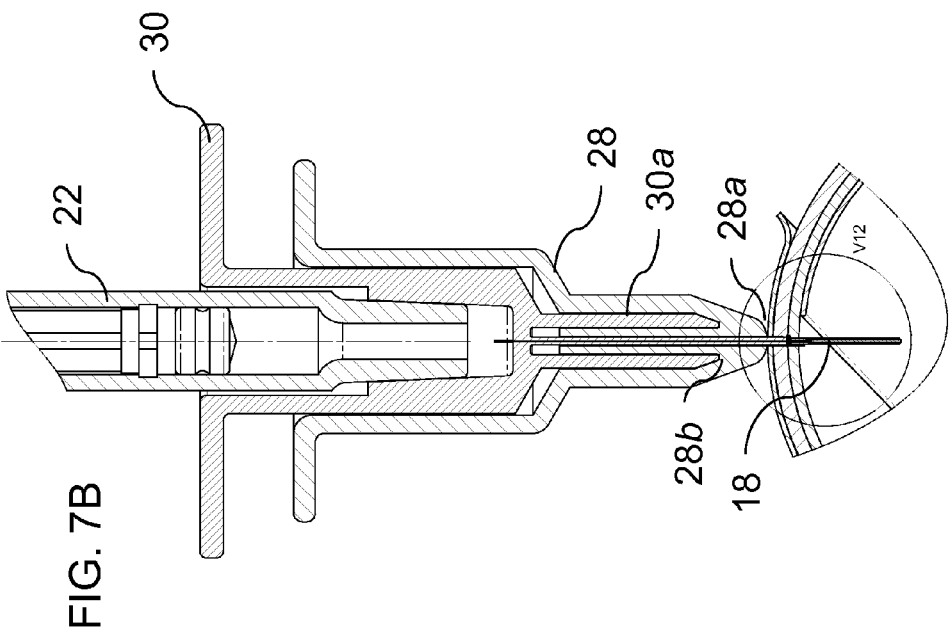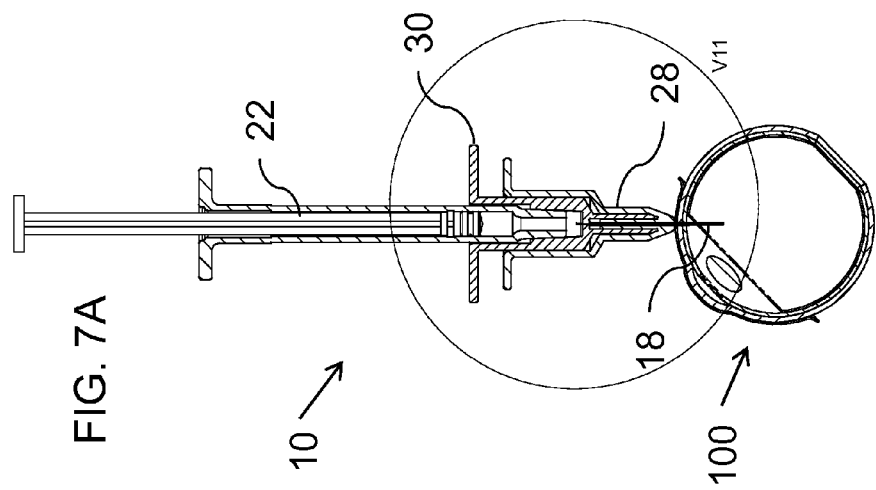

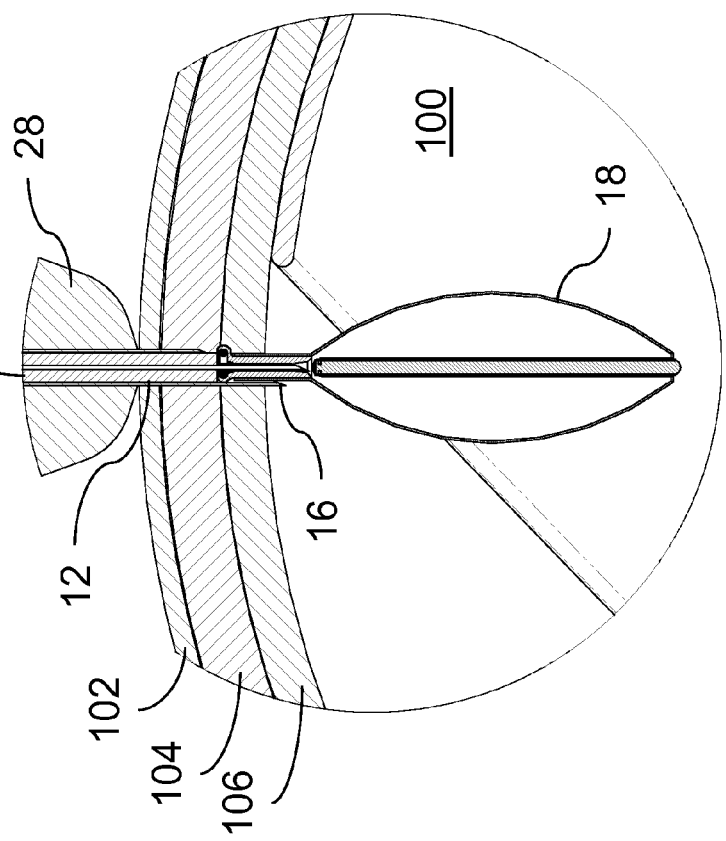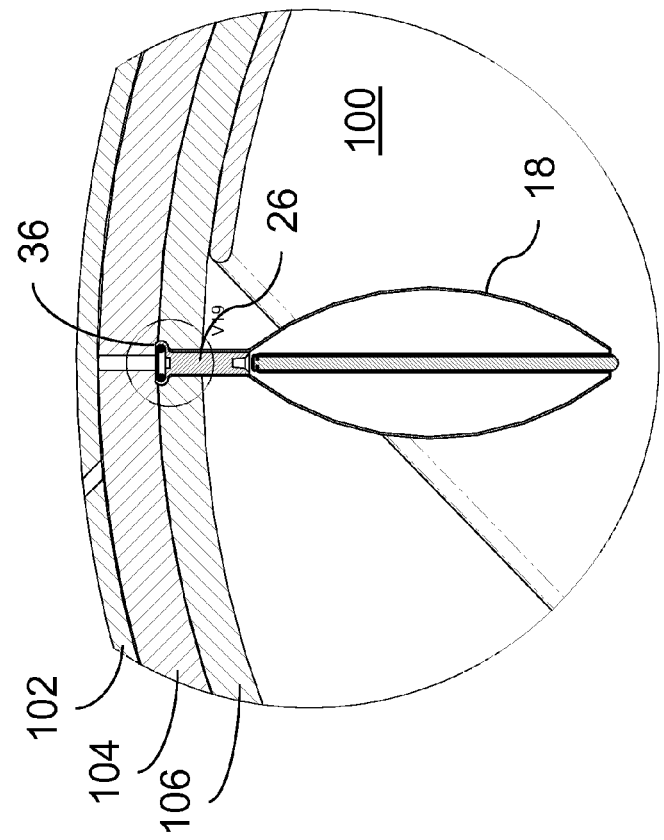

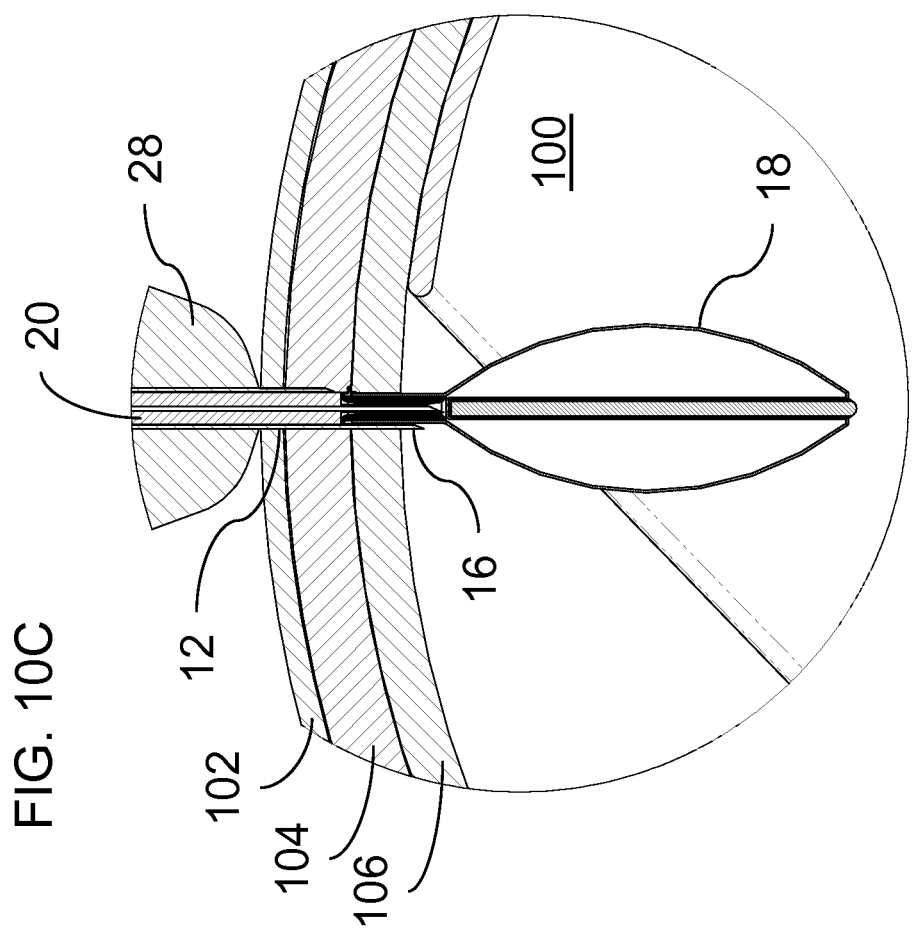

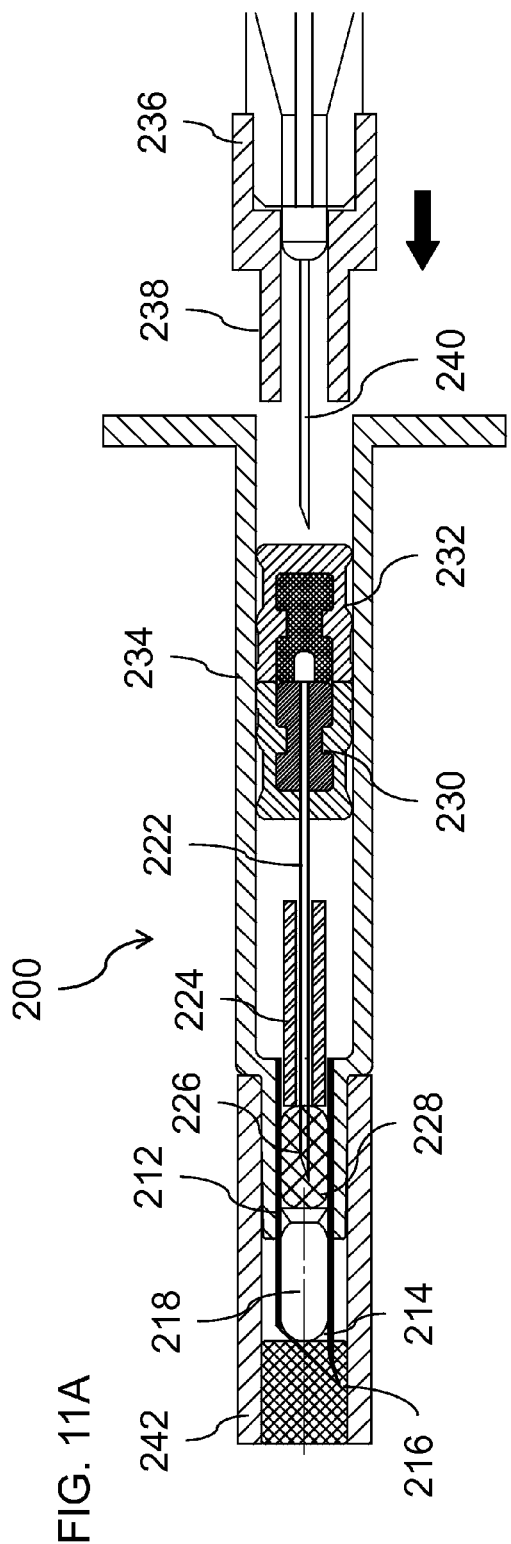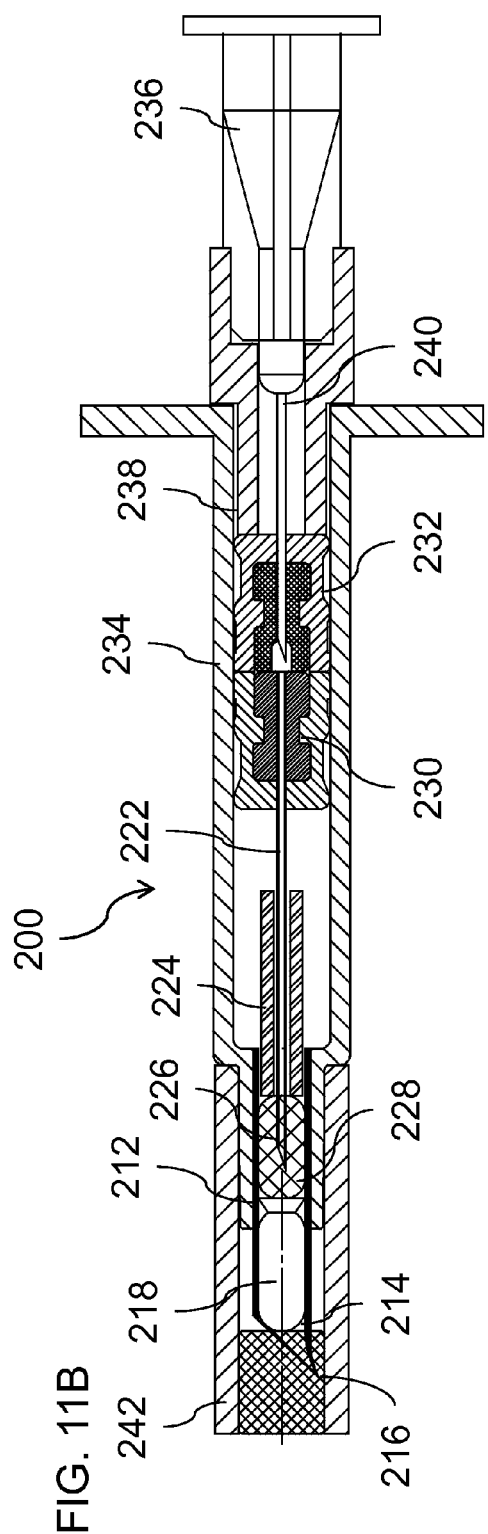

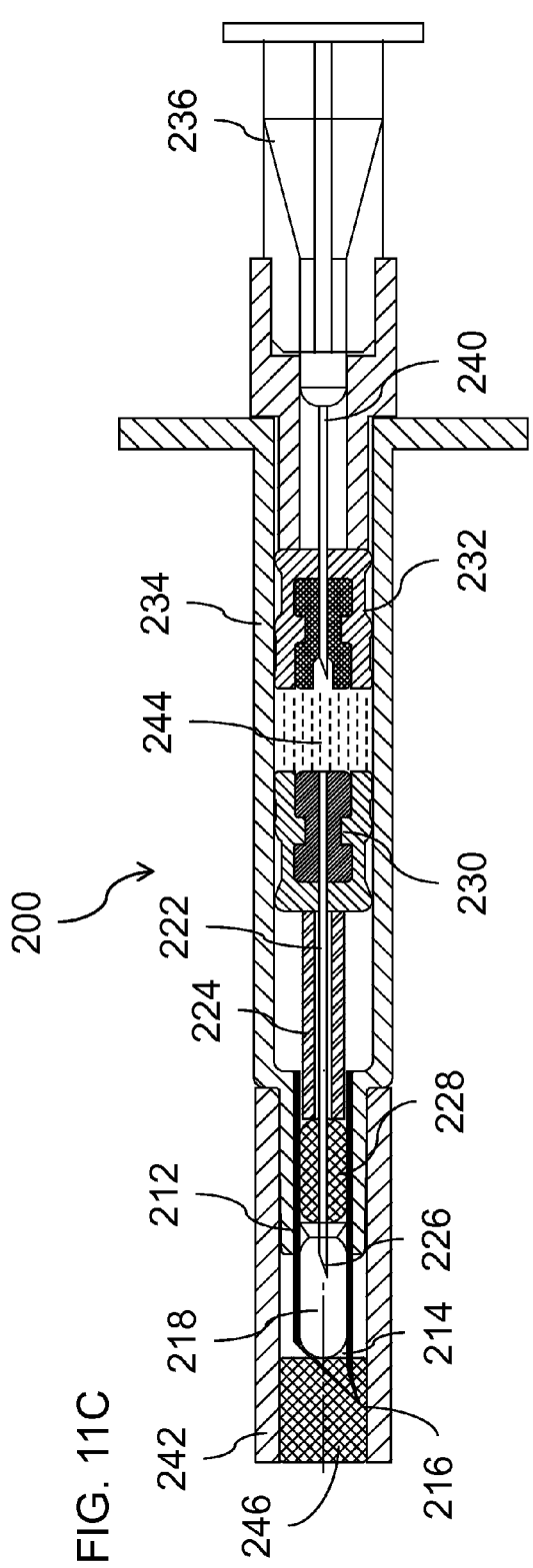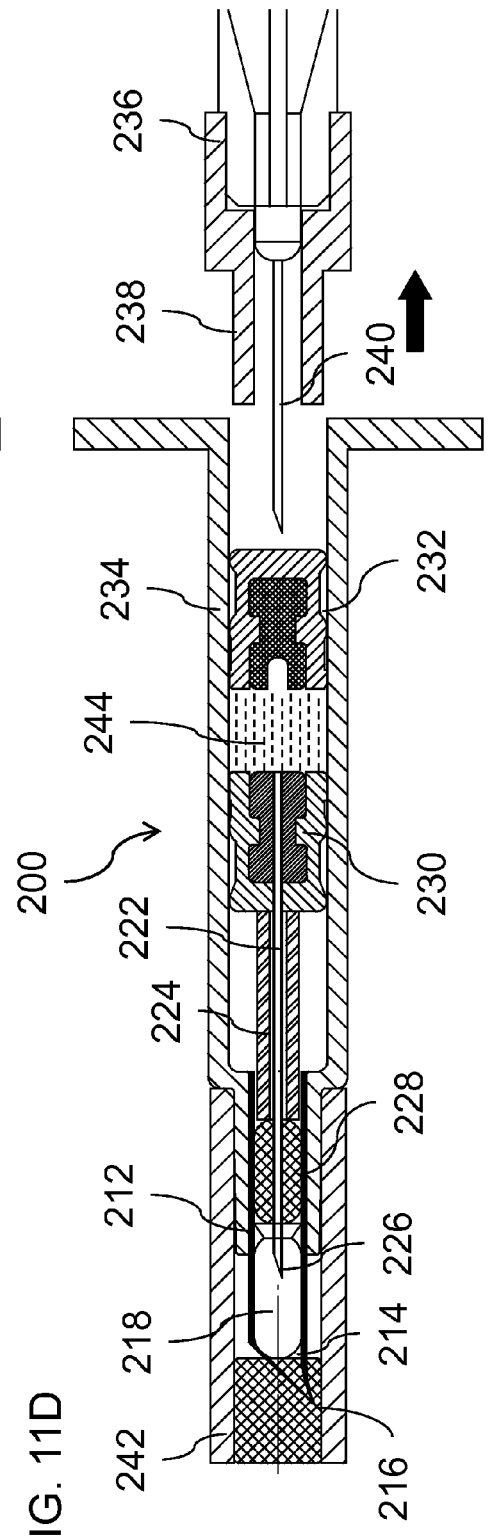

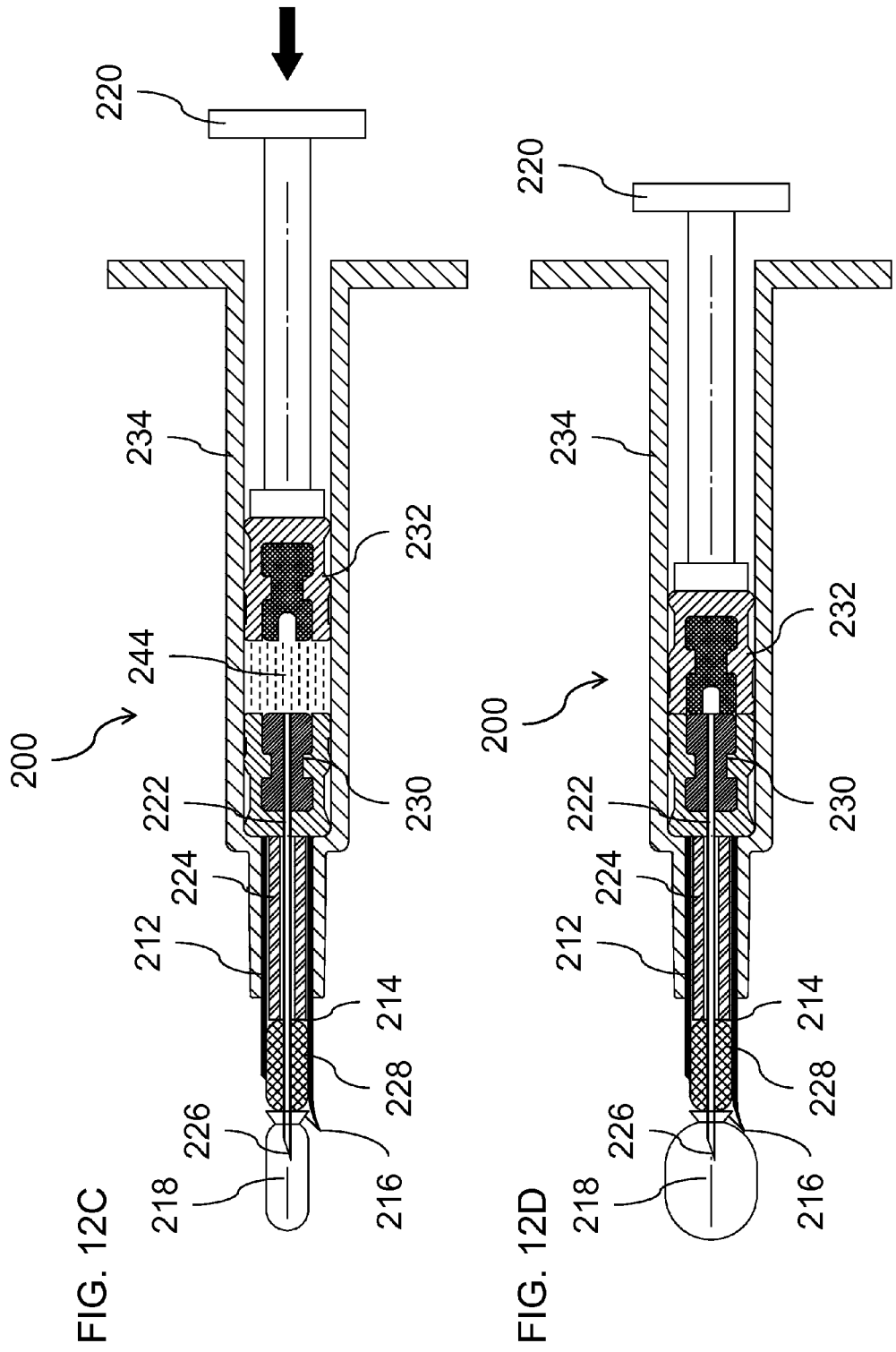

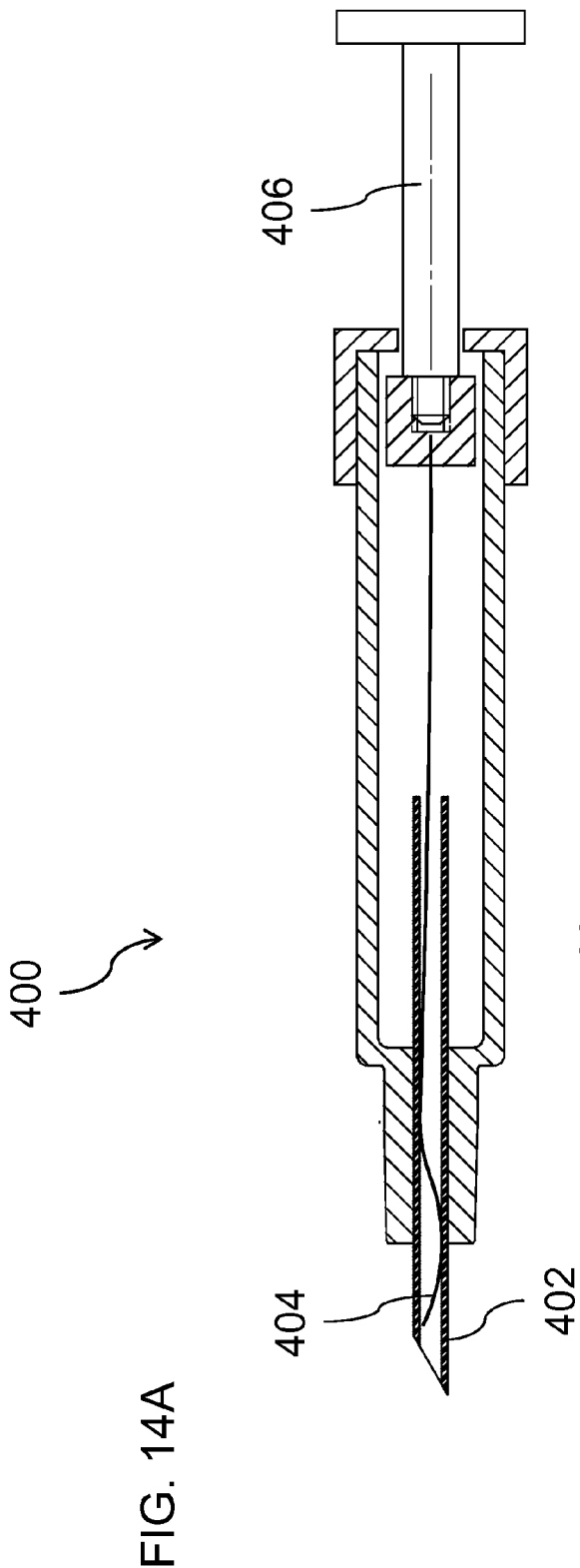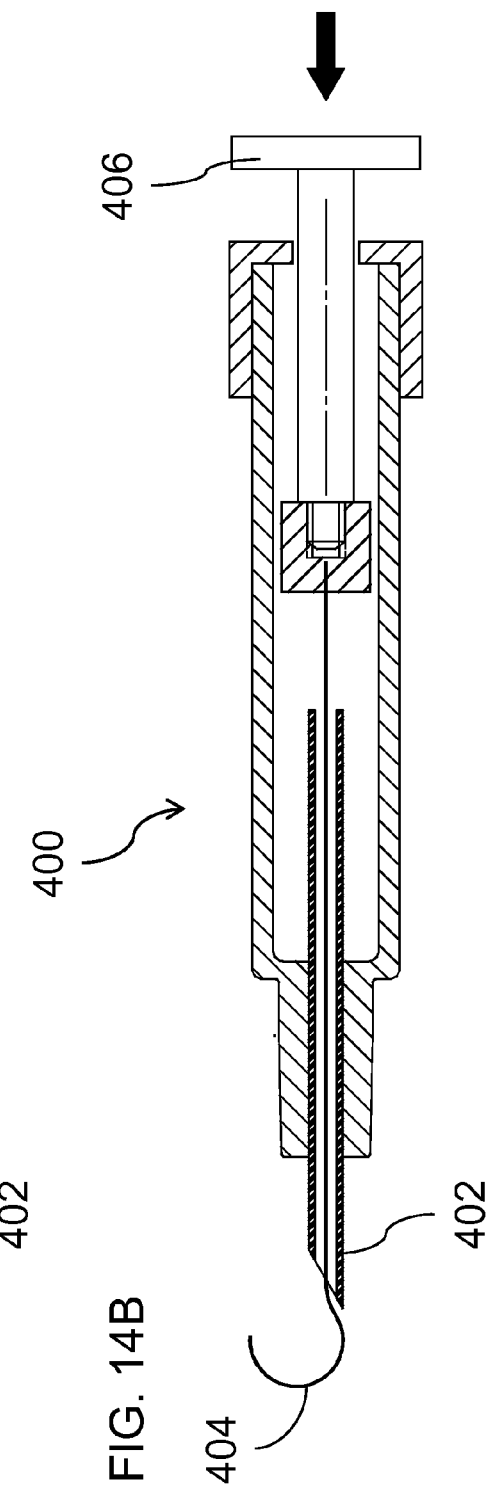
FIG. 14A
FIG. 14B

MINIATURE IMPLANTED DRUG DELIVERY DEVICES AND INSERTER SYSTEMS FOR INTRODUCING SUCH DEVICES

FIELD AND BACKGROUND OF THE INVENTION

The present invention relates to miniature drug delivery devices and, in particular, it concerns drug delivery devices with particularly low flow rates, and inserter systems for introducing such devices into the body.

It is known to provide an implantable device which delivers a drug slowly over a period of time. This approach avoids problems of patient compliance, and provides particular advantages where delivery of a drug to a specific target location allows use of much lower overall dosage than would be required for systemic delivery, possibly avoiding undesirable side effects.

In some cases, slow drug delivery is achieved by providing a drug is dispersed in a matrix of resorbable material and is gradually released as the matrix breaks down in the body. Examples of this approach may be found in U.S. Pat. Nos. 4,351,337 and 4,450,150 to Sidman. This approach typically does not achieve highly uniform drug release rates, and is not suitable for drugs which must be delivered in a liquid form or which have high diffusion rates through the matrix materials.

Examples of implantable devices for delivery of liquid drugs include, but are not limited to, U.S. Pat. Nos. 5,163,920, 4,428,397, 4,820,273, 5,061,242, 5,993,414, 6,183,461 and 5,836,935.

Certain potential applications of such devices impose particularly demanding conditions. For example, ocular applications pose a challenge as to how to anchor an implanted device so that it does not drift within the internal cavity of the eye. Furthermore, the procedure for introducing and anchoring a highly miniature drug delivery device is difficult to perform reliably and safely.

There is therefore a need for inserter systems for introducing and anchoring miniature drug delivery devices into a body structure such as the eye.

SUMMARY OF THE INVENTION

The present invention is a system and method for introducing miniature drug delivery devices. The invention also provides various structures for such miniature drug delivery devices.

According to the teachings of an embodiment of the present invention there is provided, a system for introducing a drug delivery device, the system comprising: (a) a hollow needle having a central channel and a tip; (b) a drug delivery device comprising a reservoir and a proximal filling port deployed to allow introduction of a volume of a liquid drug into the reservoir to be released over a period of time, the drug delivery device being deployed within the central channel of the hollow needle; (c) a plunger displaceable so as to push the drug delivery device along the central channel and beyond the tip of the hollow needle; and (d) a liquid injection device including a filling needle extending within the central channel of the hollow needle for engaging the filling port so as to allow filling of the reservoir after at least part of the reservoir has been advanced beyond the hollow needle, such that, when the tip of the hollow needle is inserted into or through a biological barrier of a body and the plunger is displaced towards the tip, the drug delivery device is advanced beyond the hollow needle for deployment within the body and filling by the liquid injection device.

According to a further feature of an embodiment of the present invention, the reservoir is an inflatable reservoir sized for deployment within the central channel when substantially empty and inflatable by filling with a liquid drug to assume a deployed size greater than dimensions of the central channel.

According to a further feature of an embodiment of the present invention, the filling needle is extends through at least part of the plunger such that the filling needle engages the filling port prior to advancing of the drug delivery device.

According to a further feature of an embodiment of the present invention, the drug delivery device deployed within the hollow needle, the plunger, the filling needle and the liquid injection device pre-filled with a quantity of a liquid drug, are preassembled into a single integrated delivery system for implanting and filling the drug delivery device within the body.

According to a further feature of an embodiment of the present invention, the tip of the hollow needle is a beveled tip terminating at a point, so as to facilitate introduction of the drug delivery device into a biological barrier without formation of a prior incision.

According to a further feature of an embodiment of the present invention, there is also provided an abutment surface surrounding at least part of the hollow needle so as to define a depth of penetration, and wherein the plunger has a predefined fully-advanced position, such that, after penetration of the tip into or through the biological barrier and advancing of the plunger, the drug delivery device extends to a predefined depth into the body.

According to a further feature of an embodiment of the present invention, the drug delivery device includes a radially expandable retention configuration configured to anchor the drug delivery device within a layer, or between layers, of the biological barrier.

According to a further feature of an embodiment of the present invention, the radially expandable retention configuration includes an expander element resiliently biased to a size greater than the central channel and temporarily compressed for insertion into the central channel.

According to a further feature of an embodiment of the present invention, the radially expandable retention configuration includes a flexible sleeve deployed around an external surface of the drug delivery device while within the hollow needle and configured to become axially compressed and radially expanded during advancing of the drug delivery device from the hollow needle.

There is also provided according to an embodiment of the present invention, a method for introducing a drug delivery device, the method comprising the steps of: (a) inserting the drug delivery device via a channel of a hollow needle through at least part of at least one layer of a biological barrier; and (b) subsequent to the inserting, filling the drug delivery device with a quantity of liquid drug via a filling needle extending within the channel of the hollow needle.

There is also provided according to an embodiment of the present invention, a system for introducing a drug delivery device, the system comprising: (a) a hollow needle having a central channel and a tip; (b) a drug delivery device comprising a reservoir for receiving a volume of a liquid drug to be released over a period of time, the drug delivery device being deployed within the central channel of the hollow needle; and (c) a plunger displaceable so as to push the drug delivery device along the central channel and beyond the tip of the hollow needle, wherein the drug delivery device includes a radially expandable retention configuration configured to anchor the drug delivery device within a layer, or between layers, of the biological barrier such that, when the tip of the hollow needle is inserted into or through a biological barrier of a body and the plunger is displaced towards the tip, the drug delivery device is advanced beyond the hollow needle and becomes anchored by the radially expandable retention configuration within a layer, or between layers, of the biological barrier.

According to a further feature of an embodiment of the present invention, the radially expandable retention configuration includes an expander element resiliently biased to a size greater than the central channel and temporarily compressed for insertion into the central channel.

According to a further feature of an embodiment of the present invention, the radially expandable retention configuration includes a flexible sleeve deployed around an external surface of the drug delivery device while within the hollow needle and configured to become axially compressed and radially expanded during advancing of the drug delivery device from the hollow needle.

There is also provided according to an embodiment of the present invention, a method for introducing a drug delivery device, the method comprising the steps of: (a) inserting the drug delivery device through at least part of at least one layer of a biological barrier; and (b) anchoring the drug delivery device within a layer, or between layers, of the biological barrier, wherein the steps of inserting and anchoring are performed sequentially by use of a single deployment system.

According to a further feature of an embodiment of the present invention, subsequent to the inserting, the drug delivery device is filled with a quantity of liquid drug, wherein the step of filling is additionally performed by use of the single deployment system.

There is also provided according to an embodiment of the present invention, a system for introducing a drug delivery device, the system comprising: (a) a hollow needle having a central channel and a beveled tip terminating at a point; (b) a drug delivery device comprising a reservoir for receiving a volume of a liquid drug to be released over a period of time, the drug delivery device being deployed within the central channel of the hollow needle; and (c) a plunger displaceable so as to push the drug delivery device along the central channel and beyond the tip of the hollow needle, such that, when the tip of the hollow needle is inserted into or through a biological barrier of a body and the plunger is displaced towards the tip, the drug delivery device is advanced beyond the hollow needle for deployment within the body.

BRIEF DESCRIPTION OF THE DRAWINGS

The invention is herein described, by way of example only, with reference to the accompanying drawings, wherein:

FIG. 1A is a side view of a system, constructed and operative according to an embodiment of the present invention, for introducing a drug delivery device through a biological barrier, illustrated here schematically as the surface of a human or animal eye;

FIG. 1B is a longitudinal cross-sectional view taken through the view of FIG. 1A;

FIGS. 3A-3C are enlarged views of a region of FIG. 1A showing an initial state and two successive states during preparation of the system for use;

FIGS. 4A and 4B are enlarged views of the region of FIG. 2 designated V2, and showing the relative positions of a filling needle and the drug delivery device corresponding to the states of FIGS. 3A and 3C, respectively;

FIGS. 5A-5C show a preferred sequence for insertion of a hollow needle of the delivery device into or through at least one layer of the biological barrier;

FIGS. 6A and 6B are views similar to FIGS. 3A-3C showing a further two successive states during advancing of the drug delivery device into or through at least one layer of the biological barrier;

FIG. 7A is a view similar to FIG. 1B corresponding to the state of FIG. 6B;

FIG. 7B is an enlarged view of the region of FIG. 7A designated V11;

FIG. 8C is a view similar to FIG. 8A after operation of a filling syringe to fill an inflatable reservoir of the drug delivery device;

FIG. 8D is a view similar to FIG. 8C after withdrawal of the deployment system, leaving the drug delivery device anchored between layers of the biological barrier and extending into the body for slow release drug delivery;

FIGS. 10A-10D are views similar to FIGS. 8A-8D, respectively, for the variant implementation of FIGS. 9A and 9B;

FIGS. 11A-11D are schematic longitudinal cross-sectional views taken through a system, constructed and operative according to an embodiment of the present invention, for introducing a drug delivery device through a biological barrier, showing a sequence of states during filling of a delivery system with a liquid drug in preparation for deployment of the drug delivery device;

FIGS. 12A-12E are schematic longitudinal cross-sectional views taken through the system of FIGS. 11A-11D, showing a sequence of states during deployment and filling of the drug delivery device;

FIGS. 14A and 14B are schematic longitudinal cross-sectional views illustrating a retrieval system for retrieving a drug delivery device according to the present invention, the retrieval system being shown in an insertion state and a retrieval state, respectively.

DESCRIPTION OF THE PREFERRED EMBODIMENTS

Figure 2:
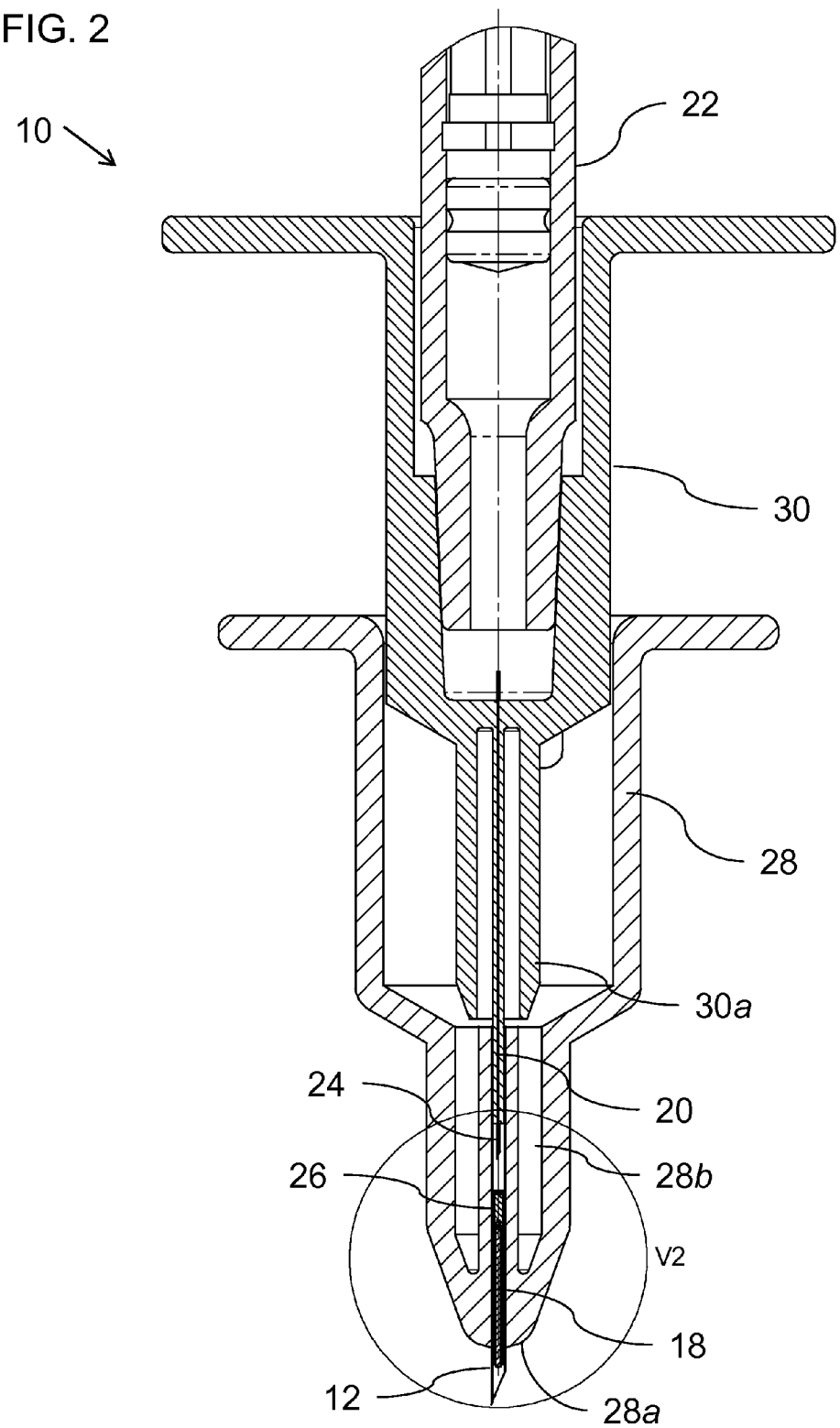
FIG. 2 is an enlarged view of the region of FIG. 1B designated V1.

The present invention is, according to a first aspect, a system and method for introducing a drug delivery device into a body. This first aspect of the invention may be implemented with a range of drug delivery devices, particularly those having a reservoir for storing a quantity of liquid drug for slow release. Other aspects of the present invention relate to devices and methods for refilling and retrieving the corresponding drug delivery devices.

The principles and operation of systems, methods and devices according to the present invention may be better understood with reference to the drawings and the accompanying description.

Referring now to the drawings, FIGS. 1A-8F illustrate the structure and operation of a first exemplary embodiment of a system, generally designated 10, and a corresponding method for introducing a drug delivery device through at least one layer of a biological barrier into a body, illustrated here with reference to a non-limiting example of the human eye 100.

In general terms, system 10 includes a hollow needle 12, having a central channel 14 and a tip 16, and a drug delivery device 18 comprising a reservoir for receiving a volume of a liquid drug to be released over a period of time. Drug delivery device 18 is small relative to the overall dimensions of system 10, and is best seen in FIGS. 4A, 4B and 8A-8D. Drug delivery device 18 is initially deployed within central channel 14 of hollow needle 12. A plunger 20 is displaceable within central channel 14 so as to push the drug delivery device beyond the tip of the hollow needle. When tip 16 of hollow needle 12 is inserted into or through a biological barrier of a body and plunger 20 is displaced towards tip 16, drug delivery device 18 is advanced beyond the hollow needle for deployment within the body, as shown in FIGS. 7A-8A.

Figure 8B:
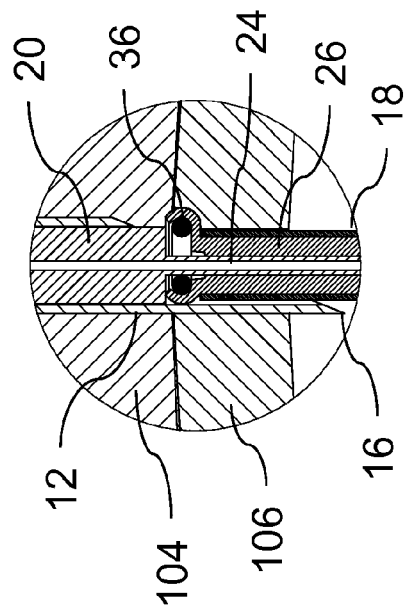
FIG. 8B is an enlarged view of the region of FIG. 8A designated V13, showing a first implementation of a radially expandable retention configuration partially deployed to anchor the drug delivery device between layers of the biological barrier.
Figure 8A:
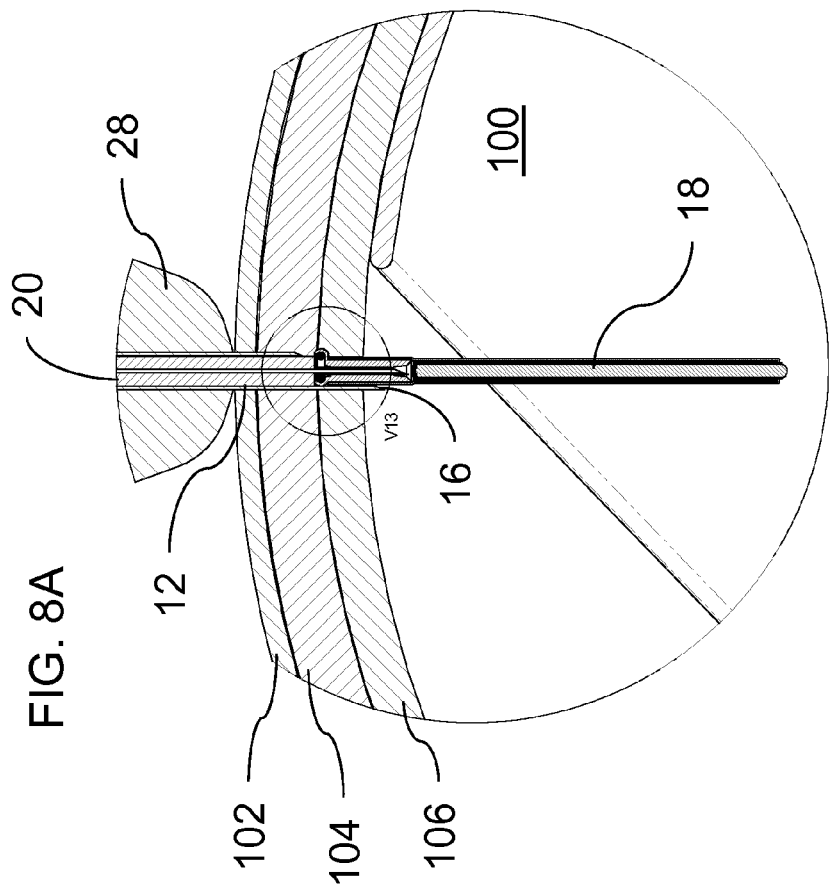
FIG. 8A is an enlarged view of the region of FIG. 7B designated V12, showing the deployed drug delivery device extending into the body.

In certain particularly preferred embodiments, the reservoir of drug delivery device 18 is an inflatable reservoir sized for deployment within central channel 14 when substantially empty, and inflatable by filling with a liquid drug to assume a deployed size greater than dimensions of the central channel. Thus, when empty, drug delivery device 18 has lateral dimensions less than the inner diameter of channel 14, as shown in FIGS. 4A & 8A. After filling, as shown in FIGS. 8C and 8D, the dimensions are increased such that at least two, and typically all three, dimensions of drug delivery device are greater than the inner diameter of channel 14.

The aforementioned approach of introducing the drug delivery device in a collapsed state and subsequently filling it facilitates introduction of the device via a much smaller needle canula than would otherwise be possible. Thus, certain preferred embodiments of the present invention employ a hollow needle 12 with internal diameter less than 2 millimeters. In certain particularly delicate applications such as ocular application, it may be preferred to employ internal diameters of less than 1 millimeter, and most preferably less than 0.5 millimeter. The deployed volume of the drug delivery device after filling is typically at least 10 times greater than the empty volume during deployment, thereby facilitating controlled delivery of relatively large quantities of drug.

According to certain particularly preferred embodiments of the present invention, introduction of the substantially empty drug delivery device and filling of the device are performed sequentially using a single deployment system, as illustrated here. Thus, in the preferred example illustrated here, system 10 includes a liquid injection device, such as a filling syringe 22 (visible in FIG. 1A), linked to a filling needle 24 (best seen in FIG. 4A). Filling needle 24 extends within central channel 14 for engaging a filling port 26 of drug delivery device 18, thereby allowing filling of the reservoir after at least part of the reservoir has been advanced beyond the hollow needle.

In the particularly preferred non-limiting example illustrated herein, filling needle 24 is integrated with plunger 20 so that the filling needle engages the filling port prior to advancing of the drug delivery device. In this case, according to certain preferred implementations, the engagement of filling needle 24 with filling port 26 is performed as a preparatory step prior to insertion of hollow needle 12 into the biological barrier. This is illustrated here with reference to the external views of FIGS. 3A-3C, which show guided retraction of a distal tip portion 28 of system 10 relative to a main block 30 of the deployment device. In the implementation shown here, the length of this initial movement is limited by a pin-and-slot inter-engagement, shown here as a pin 32 of main block 30 which is engaged in a shaped slot 34 formed in distal tip portion 28. The resulting engagement of filling needle 24 with filling port 26 is shown in FIG. 4B.

In a particularly preferred implementation, drug delivery device 18 is introduced and filled sequentially by a single integrated delivery system. Thus, the delivery system includes hollow needle 12, plunger 20, filling needle 24 and filling syringe 22, pre-filled with a quantity of a liquid drug, as illustrated in FIG. 1B.

Turning now to additional features of the preferred exemplary embodiment of FIGS. 1A-8F, needle tip 16 is illustrated in the drawings as being a beveled tip which provides a sharp point. Such an embodiment allows the entire procedure, from initial penetration of the tissue through deployment and filling of the drug delivery device, to be performed using the system of the invention without prior preparation of the insertion site. It should be noted however that alternative implementations may employ a flat-ended or otherwise blunt hollow needle 12, and rely upon a separately made prior incision, as is known in various other procedures, particularly in the field of ocular procedures where a self-sealing flap may in some cases be cut more easily with a flat cutting tool.

In the case of a pointed needle tip, a preferred sequence for insertion of needle tip 16 is illustrated schematically in FIGS. 5A-5C. According to this sequence, initial penetration of needle tip 16 is performed while the device is significantly inclined relative to the local perpendicular to the tissue surface so that the needle tip penetrates through the outer tissue layers as an oblique angle (FIG. 5B). The device is then straightened to an upright position relative to the local tissue surface (FIG. 5C) prior to completion of the drug delivery device insertion. Without in any way limiting the scope of the invention, the aforementioned angular motion is believed to generate relative lateral displacement between the outer layers of the layered tissue. As a result, after removal of the inserter device, elastic return of the tissue to its original position tends to result in the penetration openings being out of alignment, thereby providing a self-sealing function.

Referring to FIG. 2, distal tip portion 28 preferably provides an abutment surface 28a surrounding at least part of hollow needle 12 so as to define a depth of penetration of the needle. Additionally, plunger 20 has a predefined fully-advanced position. In the example illustrated here, plunger 20 is integrated with main block 30, which also features a forward projection 30a configured to enter a corresponding recess 28b in the rear of distal tip portion 28. Forward projection 30a is here shown as a cylindrical tube and recess 28b as a corresponding cylindrical recess. These structures define a fully advanced position of main block 30, and hence also of plunger 20, relative to distal tip portion 28, and also provides concentric guiding surfaces that help to maintain alignment of the components during use. The combined effect of the depth-limiting abutment surface 28a and the predefined range of motion of plunger 20 is to predefine an insertion depth to which drug delivery device 18 extends into the body once deployed, as illustrated in FIG. 7B.

According to another aspect of certain preferred embodiments of the present invention, drug delivery device 18 includes a radially expandable retention configuration 36 configured to anchor the drug delivery device within a layer, or between layers, of the biological barrier. According to a first implementation of this feature, as illustrated in FIGS. 8B and 8D, radially expandable retention configuration 36 includes an expander element resiliently biased to a size greater than the central channel and temporarily compressed for insertion into the central channel. The expander element is typically a C-shaped resilient partial-ring which is squeezed closed or otherwise compressed for insertion within central channel 14, and which returns resiliently to an oversize diameter as it emerges from tip 16.

In the example of ocular deployment as exemplified in the drawings, the structure of the biological barrier of eye 100 is made up of a number of different layers, here designated schematically as layers 102, 104 and 106, corresponding to the conjunctiva, sclera and choroid, respectively. In this case, it is particularly preferred that the length of hollow needle 12 projecting from abutment surface 28a is chosen to correspond roughly to the depth of the boundary between two of the layers 104 and 106, so that expandable retention configuration 36 becomes lodged between layers 104 and 106 when deployed. Radially expandable retention configuration 36 then serves to anchor one end of drug delivery device 18 between the layers after removal of the delivery system, as shown FIG. 8D.

Figure 8E:
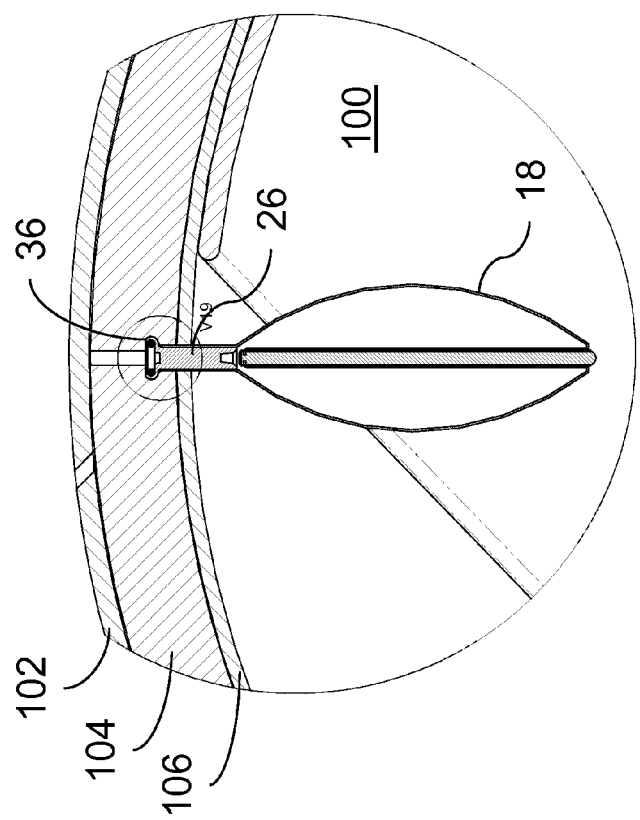
FIG. 8E is a view similar to FIG. 8D illustrating a variant implementation of an anchoring configuration for anchoring the drug delivery device of the above embodiment in the layers of the biological barrier.
Figure 8F:
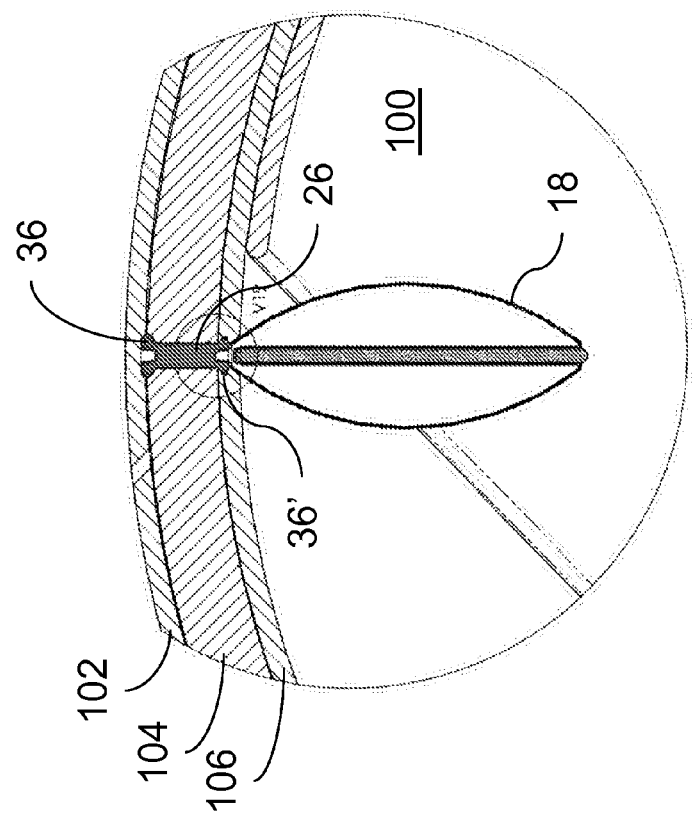
FIG. 8F is a view similar to FIG. 8D illustrating a further variant implementation of an anchoring configuration for anchoring the drug delivery device of the above embodiment in the layers of the biological barrier.
Figure 9B:
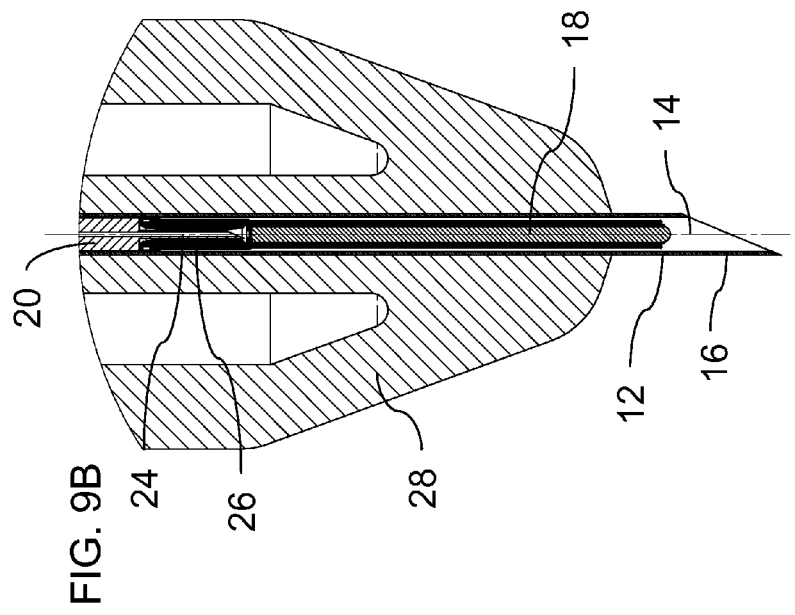
FIGS. 9A and 9B are views similar to FIGS. 4A and 4B, respectively, illustrating a variant implementation of the drug delivery device with an alternative implementation of the radially expandable retention configuration.
Figure 9A:
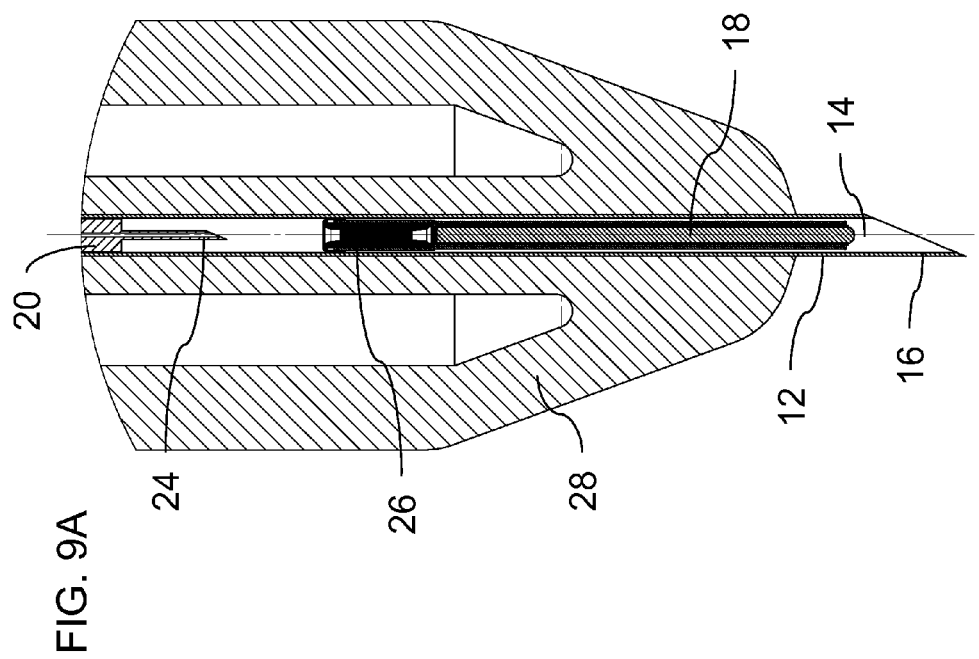

FIG. 8E shows a variant implementation in which the depth of penetration is chosen such that radially expandable retention configuration lodges itself within the thickness of the sclera layer 104, thereby relying on the relatively high structural strength of the sclera for positive anchoring of the device. FIG. 8F shows a further variant in which two radially expandable retention elements 36 and 36' are spaced apart to provide two-location anchoring, preferably corresponding to the inner and outer surfaces of the sclera 104.

Figure 10B:
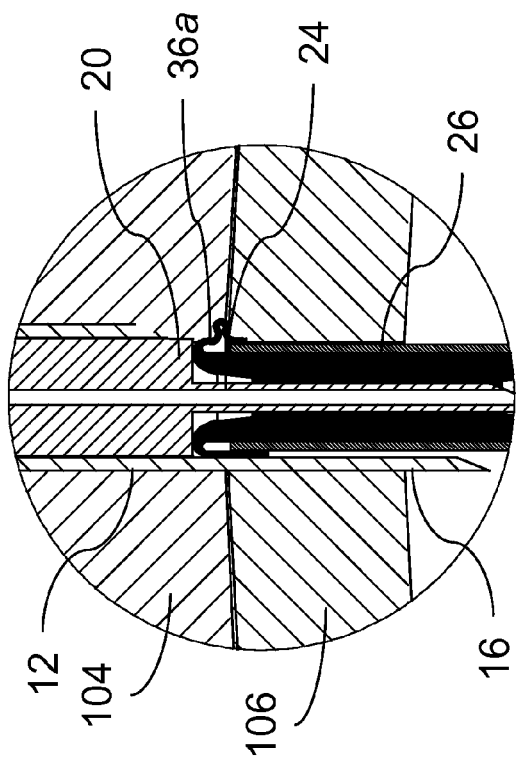
Figure 10A:
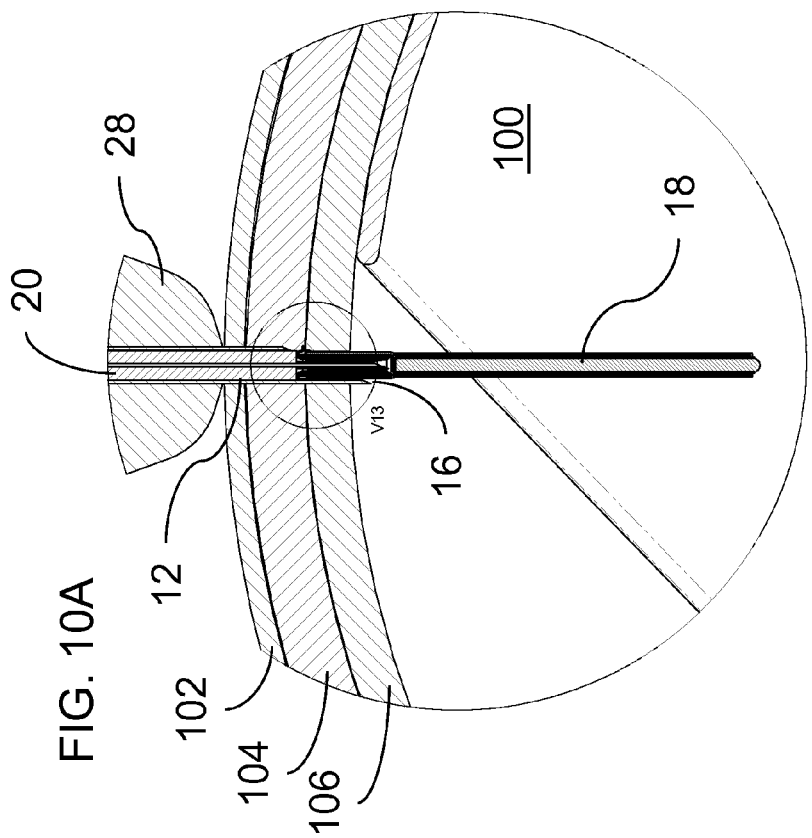
Figure 10D:
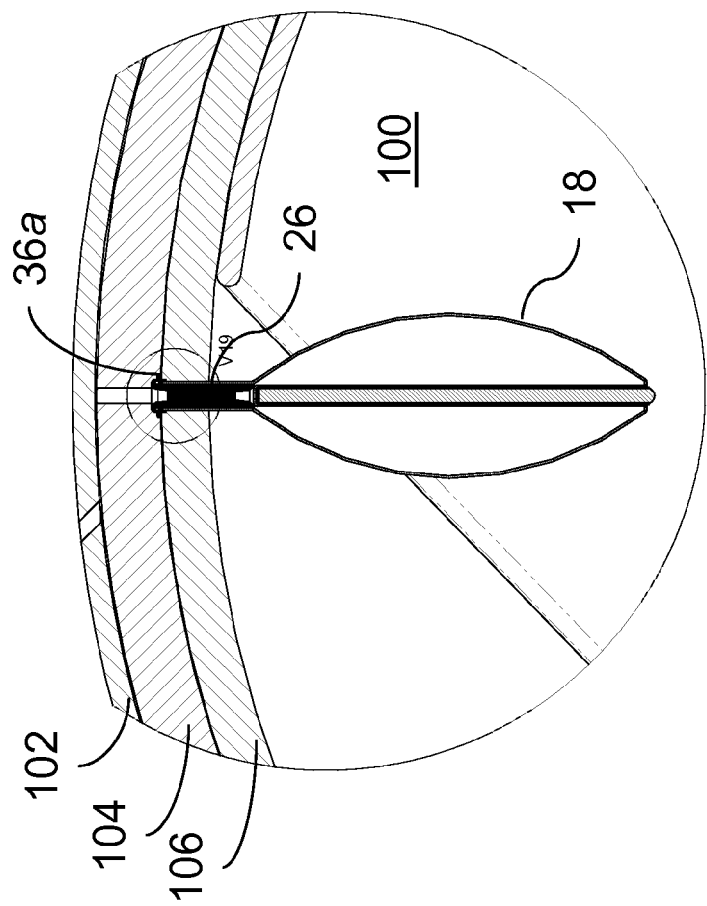
Figure 10E:
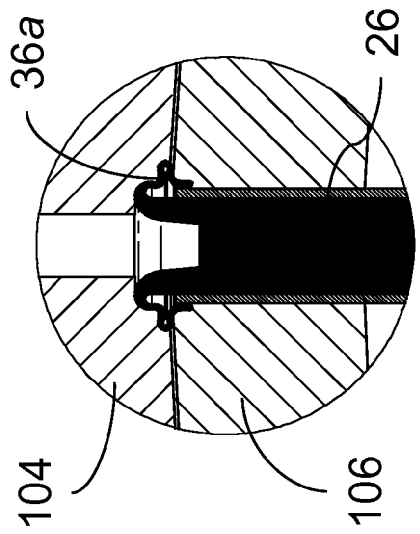
FIG. 10E is an enlarged view of the region of FIG. 10D designated V19, illustrating the deployed state of the alternative implementation of the radially expandable retention configuration.

Referring parenthetically to FIGS. 9A-10E, these illustrate an alternative implementation of a radially expandable retention element in which the retention element includes a flexible sleeve 36a, best seen in FIGS. 10B and 10E. Flexible sleeve 36a is deployed around an external surface of the drug delivery device while within the hollow needle, and is made from sufficiently loose and flexible material that it tends to become caught on surrounding tissue as it emerges from hollow needle 12, thereby becoming axially compressed and radially expanded (i.e., forming an outward fold or "kink") during advancing of the drug delivery device from the hollow needle. Hollow needle 12 is inserted through layer 102 and at least part of layer 104, so that flexible sleeve 36a does not interact with those layers as device 18 is advanced into the tissue. When flexible sleeve 36a starts to leave needle 12 and encounters the tissue layer 106, the sleeve becomes caught on the tissue and slides along the outside of the drug delivery device. The bunching up of the sleeve material forms the aforementioned outward fold which tends to be caught between the layers of the biological barrier and provide the aforementioned anchoring effect. In all other respects, the device of FIGS. 9A-10E may be implemented in a system and method similar to those described in FIGS. 1A-8D.

Although shown here in the context of a multi-layer biological barrier, it should be noted that similar structures may be used to anchor the device of the present invention relative to a single layer barrier, or relative to other body structures, all as will be clear to a person having ordinary skill in the art according to the particular intended application.

Regarding drug delivery device 18 itself, this aspect of the present invention may be implemented with a wide range of drug delivery devices that are based on an inflatable bladder-type reservoir for storing and slowly releasing a quantity of a liquid drug composition or the like. A number of non-limiting examples of suitable drug delivery devices may be found in co-pending international application publication no. WO 2011/101833 filed Feb. 22, 2011, and related U.S. patent application Ser. No. 13/430,730, filed 27 Mar. 2012, which do not constitute prior art. These examples regulate flow rates for release of the liquid drug by employing fine channels formed in facing surfaces between two parts of the drug delivery device, preferably also provide pressure-responsive regulation of the flow rate, or by use of a flow path passing through a porous block which may be biodegradable.

The operation of system 10 will now be clearly understood. In preparation for use, distal tip portion 28 is first retracted towards main block 30 to engage filling needle 24 with filling port 26, as illustrated in FIGS. 3A-3C and 4A-4B. Needle tip 16 is then introduced as illustrated in FIGS. 5A-5C, or via a preformed incision, and main block 30 is advanced as shown in FIGS. 6A-6B to deploy drug delivery device within the body, as shown in FIG. 7A-8A. During introduction of the device, the radially expandable retention configuration 36 or 36a is at least partially deployed (FIGS. 8B and 10B). The piston of filling syringe 22 is then advanced so as to fill the reservoir of drug delivery device 18 (FIGS. 8C and 10C), and the deployment system is withdrawn, leaving the deployed and operating drug delivery device 18 anchored between layers of the biological barrier as shown in FIGS. 8D and 10D.

Turning now to FIGS. 11A-12E, there is shown a variant embodiment of a system, generally designated 200 for introducing a drug delivery device through at least one layer of a biological barrier into a body, such as the human eye. System 200 is generally analogous in structure and function to system 10 described above.

Thus, in general terms, similar to system 10, system 200 includes a hollow needle 212, having a central channel 214 and a tip 216, and a drug delivery device 218 which includes a reservoir for receiving a volume of a liquid drug to be released over a period of time. Drug delivery device 218 is small relative to the overall dimensions of system 200 and is initially deployed within central channel 214 of hollow needle 212.

One distinguishing feature of system 200 is that sequential deployment and filling of drug delivery device 218 are effected by a single continuous motion of a manually operated actuator 220, thereby simplifying operation of the system, as will now be detailed.

As seen in FIG. 11A, system 200 includes a filling needle 222 which extends through a hollow spacer 224 to a penetrating tip 226 which is initially embedded in a seal 228. The opposite end of filling needle 222 passes through, and is integrated with, a first piston 230 which can slide in sealing contact with the inner bore of a syringe body 234. A second piston 232, also in sealing contact with the inner bore of syringe body 234, is initially in close contact with first piston 230.

Prior to use, system 200 is prepared by introduction of the liquid drug to a storage volume defined within syringe body 234 between pistons 230 and 232. A non-limiting exemplary implementation of this preparatory process is illustrated in FIGS. 11A-11D. In the implementation shown here, an adapter 236 includes alignment features 238 for centering an adapter needle 240 within the bore of syringe body 234 such that, as the adapter is inserted as shown in FIGS. 11A and 11B, the tip of adapter needle 240 penetrates an elastomer septum of second piston 232 to reach a small recess between the two pistons. The required quantity of drug is then introduced via adapter 236, typically by attachment of a standard syringe (not shown) to the rear of the adapter. Introduction of the liquid drug forces the two pistons apart, advancing first piston 230 to the position illustrated in FIG. 11C to make space for the drug which occupies volume 244. This motion of piston 230 causes a corresponding advancing of filling needle 222 so that the penetrating tip 226 emerges from seal 228 and penetrates through the septum (not shown) of drug delivery device 218. Drug delivery device 218 is prevented from moving at this stage by the presence of a protective cap 242 which includes an elastomer stopper 246. Adapter 236 is then removed (FIG. 11D), leaving system 200 ready for use.

Figures 12A, 12B:
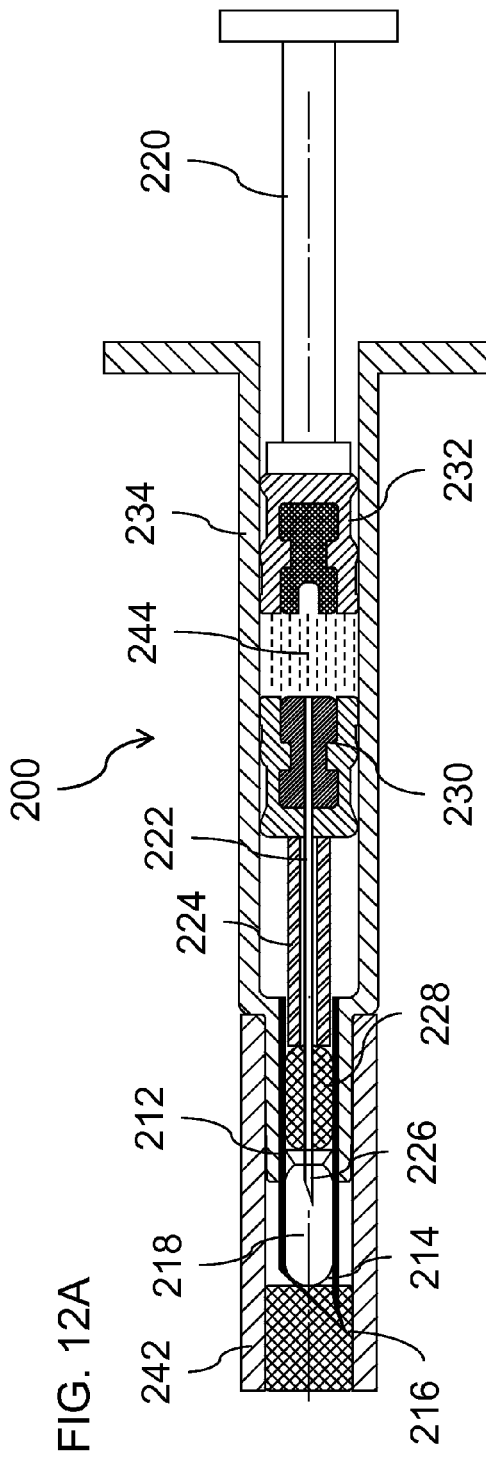
Figure 12E:
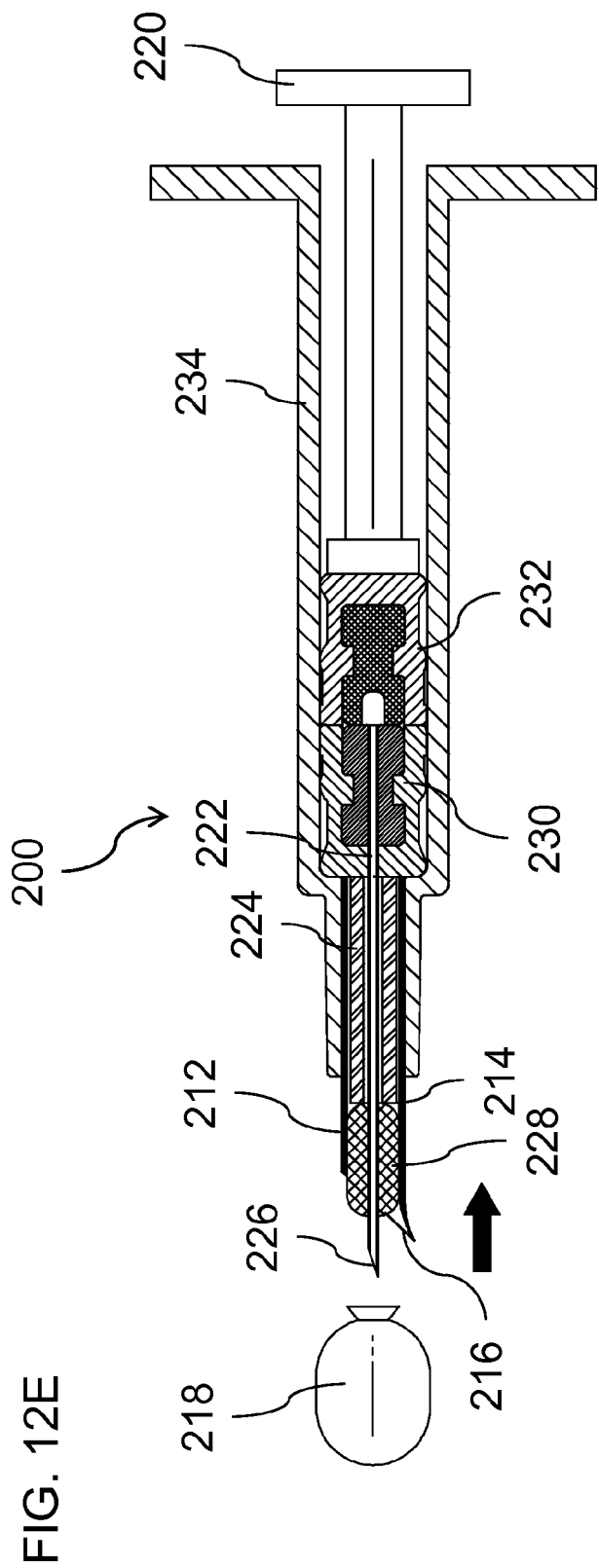

For deployment of the drug delivery device through a biological membrane, a manually operated actuator 220, shown here in a preferred embodiment in the form of a plunger, is attached to second piston 232, as illustrated in FIG. 12A, and protective cap 242 is removed, leaving the system as illustrated in FIG. 12B. Tip 216 of hollow needle 212 is then inserted into the biological barrier, preferably in a manner similar to that described above with reference to FIGS. 5A-5C.

Manual pressure is then applied to plunger 220 to advance it along the body of syringe 234. Pressure applied by the plunger to piston 232 applies pressure to the liquid drug which in turn applies pressure to piston 230. This pressure advances piston 230, which presses against spacer 224, thereby advancing spacer 224, seal 228 and drug delivery device 218 along hollow needle 212 until drug delivery device 218 is deployed in the desired position beyond the tip of the deployment system (FIG. 12C). Thus plunger 220, piston 232, liquid-filled volume 244, piston 230, spacer 224 and seal 228 all function together as a compound plunger with which filling needle 222 is integrated. Until this point, drug delivery device 218 was prevented from inflating due to the walls of hollow needle 212 surrounding it. After leaving the confines of hollow needle 212, and with piston 230 reaching a stop position at the end of the bore of syringe 234, further displacement of plunger 220 and piston 232 forces the liquid drug from volume 244 along filling needle 222, thereby inflating the reservoir of drug delivery device 218, as shown in FIG. 12D. Thus, both insertion of the drug delivery device and filling of the drug delivery device with liquid drug are both achieved sequentially by the advancing of plunger 220 unidirectionally along its range of motion. The deployment system 200 is then withdrawn, leaving drug delivery device 218 in position for slow delivery of the drug over a period of time.

It should be noted that system 200 has been shown here schematically, and has only been detailed to an extent necessary to appreciate the distinctive features of this embodiment, while numerous other features that are similar to features of the embodiment described above have not been detailed here. For example, drug delivery device 218 preferably features one or more radially expandable retention elements, such as is described above with reference to FIG. 8A-8D, 8E, 8F or 10A-10E. Similarly, the distal end of syringe 234 which surrounds hollow needle 212 preferably defines abutment surfaces for defining the extent of penetration of hollow needle 212. Except where explicitly stated or self-evident otherwise, it should be understood that features described herein with reference to one embodiment may also be implemented in the context of other embodiments of the present invention.

Figure 13:
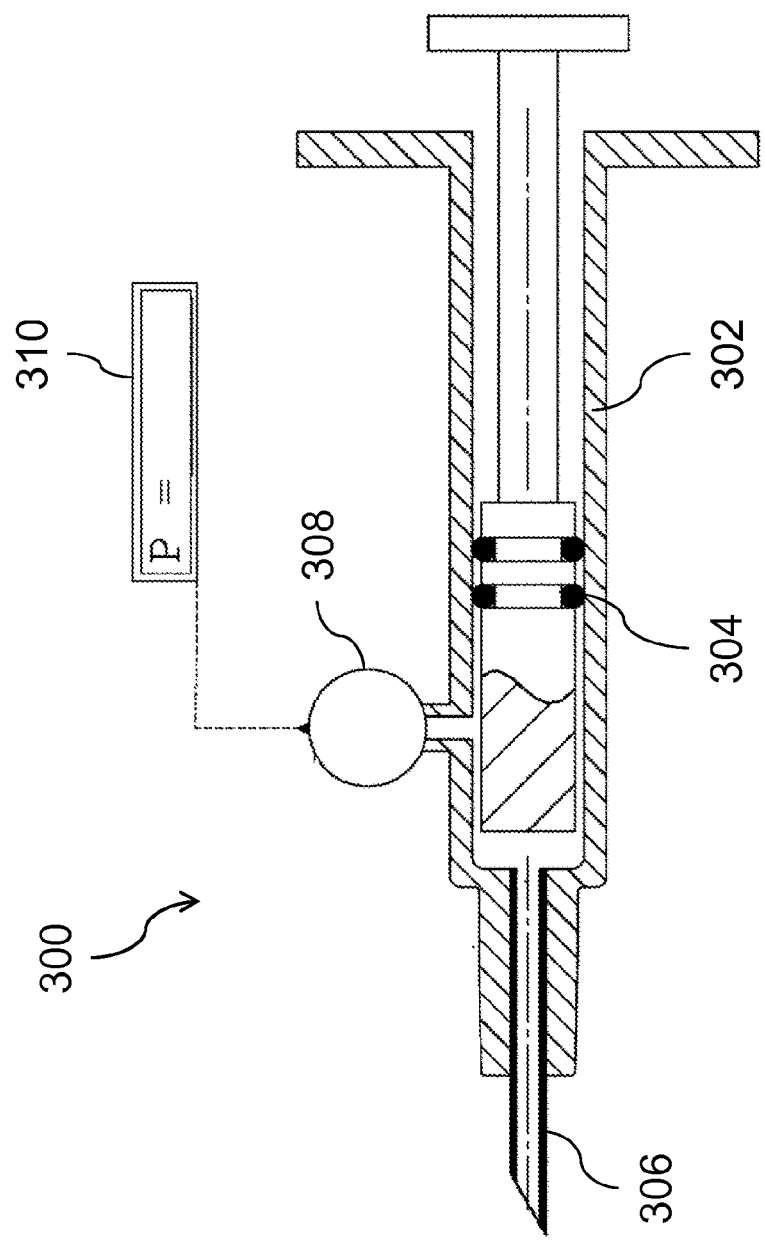
FIG. 13 is a schematic representation of a device according to an aspect of the present invention for refilling a drug delivery device according to the present invention.

Turning now to FIG. 13, as mentioned earlier, certain particularly preferred embodiments of the present invention provide an option for refilling of the drug delivery device deployed according to the present invention in situ. Given the very small dimensions of the drug delivery device according to certain implementations of the present invention, there is a need to ensure that a refilling needle has been correctly inserted through the refilling septum of the drug delivery device, and remains correctly inserted throughout the refilling process. There is also a need to assess the quantity of the drug present in the reservoir so as to ensure sufficient drug is provided without dangerously over-filling the device. For this purpose, the present invention provides a refilling device, generally designated 300, constructed and operative according to a further feature of an embodiment of the present invention. Refilling device 300 is shown here schematically as a syringe type device including a syringe body 302 and a plunger 304 for delivering refill drug to the drug delivery device via a refill needle 306. Additionally, device 300 includes a pressure measurement arrangement 308 deployed for measuring the fluid pressure within the syringe during operation, and a processing system 310 having a processor, a data storage device and a display, connected so as to receive the fluid pressure measurements. Monitoring of the pressure after insertion of the device and prior to injection of its contents provides a reliable verification that the needle has correctly reached the elevated-pressure inner volume of the drug storage reservoir. A known and pre-calibrated profile mapping pressure to reservoir content may also facilitate evaluation of the degree of filling of the reservoir during the refilling process. Processing system 310 preferably stores a look-up table or parametrically defined model, preferably empirically derived, indicating the current reservoir contents as a function of the measured pressure within the syringe under zero-flow conditions. Processing system thus preferably translates measured pressure into a visually displayed indication of the current reservoir content. The processor preferably also provides a warning function if the sensed pressure drops below the expected value, indicating that the refill needle 306 may not be correctly inserted into the drug delivery device or may have become dislodged. Most preferably, the refilling device 300 also features a safety valve, deployed for example as part of plunger 304, which ensures release of the contained drug outside the patient in the event that the pressure exceeds a maximum allowed threshold value which might lead to a risk of damaging the drug delivery device.

Turning now to FIGS. 14A and 14B, there is shown a preferred embodiment of a retrieval device, generally designated 400, for retrieving the drug delivery devices of the present invention. Retrieval device 400 preferably features a fine needle 402, similar to the refilling needles described above, which is sufficiently fine to be inserted through the refilling port of the drug delivery device. Inside needle 402 is a resilient wire 404 pre-formed into a hook or otherwise curled form, but maintained in a straightened configuration by the small diameter inner lumen of needle 402. An actuator 406 is manually deployable to selectively advance resilient wire 404 so as to extend beyond needle 402.

In use, needle 402 is introduced into the drug delivery device via the refilling port while resilient wire 404 is in its straightened state. Wire 404 is then advanced within the device, forming its hooked or otherwise curled form within the device, preferably so as to become anchored on or tangled around internal features of the drug delivery device. The retrieval device can then be removed, drawing after it the drug delivery device.

It will now be appreciated that various embodiments of the present invention provides a number of significant advantages over existing options in the field of implantable devices for delivering liquid medications. In particular, certain embodiments of the present invention provide one or more of the following functions:

- Insertion of the drug delivery device through at least part of at least one layer of a biological barrier and anchoring of the drug delivery device within a layer, or between layers, of the biological barrier, where both the inserting and anchoring are performed sequentially by use of a single deployment system.
- Insertion of the drug delivery device through at least part of at least one layer of a biological barrier and subsequent filling of the drug delivery device with a quantity of liquid drug, wherein both the inserting and filling are performed sequentially by use of a single deployment system.
- Introduction of the drug delivery device by a straightforward injection technique via a needle of diameter smaller than the dimensions of the liquid reservoir after filling.
- Introduction of the drug delivery device by a deployment device which predefines the depth of insertion, thereby facilitating consistent results without requiring unusual skill in the deployment process.

It will be appreciated that the above descriptions are intended only to serve as examples, and that many other embodiments are possible within the scope of the present invention as defined in the appended claims.

What is claimed is:

1. A system for introducing a drug delivery device, the system comprising:
   (a) a hollow needle having a central channel and a tip;
   (b) a drug delivery device comprising a reservoir and a proximal filling port deployed to allow introduction of a liquid drug into said reservoir to be released over a period of time, said drug delivery device being deployed within said central channel of said hollow needle;
   (c) a plunger displaceable so as to push said drug delivery device along said central channel so as to project beyond said tip of said hollow needle; and
   (d) a liquid injection device including a contained volume for receiving a quantity of the liquid drug and a filling needle in fluid communication with said contained volume and extending within said central channel of said hollow needle for engaging said filling port,
wherein said liquid injection device is configured such that, when said tip of said hollow needle is inserted into or through a biological barrier of a body, and at least part of said reservoir is advanced beyond said hollow needle, said liquid injection device is operative to deliver the liquid drug from said contained volume through said filling needle while said filling needle is located at least partially within said hollow needle so as to fill said reservoir prior to withdrawal of said hollow needle.

2. The system of claim 1, wherein said reservoir is an inflatable reservoir sized for deployment within said central channel when substantially empty and inflatable by filling with the liquid drug to assume a deployed size greater than dimensions of said central channel.

3. The system of claim 1, wherein said filling needle extends through at least part of said plunger such that said filling needle engages said filling port prior to advancing of said drug delivery device.

4. The system of claim 1, wherein said drug delivery device deployed within said hollow needle, said plunger and said liquid injection device filled with a quantity of a liquid drug, are assembled prior to use into a single integrated delivery system for implanting and filling said drug delivery device within the body.

5. The system of claim 1, wherein said tip of said hollow needle is a beveled tip terminating at a point, so as to facilitate introduction of said drug delivery device into a biological barrier without formation of a prior incision.

6. The system of claim 1, further comprising an abutment surface surrounding at least part of said hollow needle so as to define a depth of penetration, and wherein said plunger has a predefined fully-advanced position, such that, after penetration of said tip into or through the biological barrier and advancing of said plunger, said drug delivery device extends to a predefined depth into the body.

7. The system of claim 1, wherein said drug delivery device includes a radially expandable retention configuration configured to anchor said drug delivery device within a layer, or between layers, of the biological barrier.

8. The system of claim 7, wherein said radially expandable retention configuration includes an expander element resiliently biased to a size greater than said central channel and temporarily compressed for insertion into said central channel.

9. The system of claim 7, wherein said radially expandable retention configuration includes a flexible sleeve deployed around an external surface of said drug delivery device while within said hollow needle and configured to become axially compressed and radially expanded during advancing of said drug delivery device from said hollow needle.

10. The system of claim 1, wherein said liquid injection device is mechanically associated with said hollow needle such that withdrawal of said hollow needle from said drug delivery device requires disconnection of said filling needle from said filling port.

\* \* \* \* \*